US008849577B2

(12) United States Patent
Ryals et al.

(10) Patent No.: US 8,849,577 B2
(45) Date of Patent: Sep. 30, 2014

(54) METHODS OF IDENTIFYING BIOCHEMICAL PATHWAYS

(75) Inventors: John A. Ryals, Chapel Hill, NC (US); Daniel P. Stevens, Chapel Hill, NC (US); Michael V. Milburn, Cary, NC (US)

(73) Assignee: Metabolon, Inc., Durham, NC (US)

( * ) Notice: Subject to any disclaimer, the term of this patent is extended or adjusted under 35 U.S.C. 154(b) by 932 days.

(21) Appl. No.: 11/901,523

(22) Filed: Sep. 17, 2007

(65) Prior Publication Data

US 2008/0161228 A1 Jul. 3, 2008

Related U.S. Application Data

(60) Provisional application No. 60/845,045, filed on Sep. 15, 2006.

(51) Int. Cl.
*G06F 19/00* (2011.01)
*G01N 33/50* (2006.01)

(52) U.S. Cl.
CPC .................. *G01N 33/5008* (2013.01)
USPC .......................................... 702/19

(58) Field of Classification Search
CPC .............. G06F 19/10; G01N 33/5079; G01N 33/5091; G01N 33/6893; G01N 33/5008; G01N 2800/304; G01N 2800/52; C12Q 1/00; C12Q 1/68
See application file for complete search history.

(56) References Cited

U.S. PATENT DOCUMENTS

| | | |
|---|---|---|
| 4,511,659 A | 4/1985 | Matson |
| 4,863,873 A | 9/1989 | Matson |
| 5,104,639 A | 4/1992 | Matson |
| 5,541,310 A | 7/1996 | Ward et al. |
| 5,565,323 A | 10/1996 | Parker et al. |
| 5,824,467 A | 10/1998 | Mascarenhas |
| 5,871,712 A | 2/1999 | Siman |
| 5,880,146 A | 3/1999 | Gillies et al. |
| 5,977,083 A | 11/1999 | Burcoglu |
| 6,004,755 A | 12/1999 | Wang |
| 6,053,866 A | 4/2000 | McLeod |
| 6,087,090 A | 7/2000 | Mascarenhas |
| 6,168,933 B1 | 1/2001 | Kaser et al. |
| 6,190,858 B1 | 2/2001 | Persaud et al. |
| 6,194,217 B1 | 2/2001 | Matson |
| 6,210,970 B1 | 4/2001 | Matson |
| 6,218,117 B1 | 4/2001 | Herrnstadt et al. |
| 6,258,605 B1 | 7/2001 | Chace |
| 6,287,790 B1 | 9/2001 | Lelievre et al. |
| 6,303,365 B1 | 10/2001 | Martin et al. |
| 6,319,668 B1 | 11/2001 | Nova et al. |
| 6,326,163 B1 | 12/2001 | Forssmann et al. |
| 6,326,164 B1 | 12/2001 | Rice et al. |
| 6,329,208 B1* | 12/2001 | Jones et al. .................. 436/173 |
| 6,344,322 B1 | 2/2002 | Polyak et al. |
| 6,350,588 B1 | 2/2002 | Roth et al. |
| 6,355,635 B1* | 3/2002 | Elliott et al. ................ 514/231.5 |
| 6,376,210 B1 | 4/2002 | Yuan |
| 6,558,955 B1 | 5/2003 | Kristal et al. |
| 6,677,160 B1 | 1/2004 | Stockman et al. |
| 6,680,203 B2 | 1/2004 | Dasseux et al. |
| 7,005,255 B2 | 2/2006 | Kaddurah-Daouk et al. |
| 7,329,489 B2 | 2/2008 | Kaddurah-Daouk et al. |
| 2002/0009740 A1 | 1/2002 | Kaddurah-Daouk et al. |
| 2002/0081626 A1 | 6/2002 | Kaddurah-Daouk et al. |
| 2002/0087275 A1* | 7/2002 | Kim et al. ...................... 702/19 |
| 2003/0124548 A1* | 7/2003 | Hatzis et al. ...................... 435/6 |
| 2003/0175979 A1* | 9/2003 | Lam et al. ...................... 436/57 |
| 2003/0229451 A1 | 12/2003 | Hamilton et al. |
| 2004/0002842 A1 | 1/2004 | Woessner et al. |
| 2004/0018500 A1 | 1/2004 | Glassbrook et al. |
| 2004/0018501 A1 | 1/2004 | Allen et al. |
| 2004/0019429 A1 | 1/2004 | Coffin et al. |
| 2004/0019430 A1 | 1/2004 | Hurban et al. |
| 2004/0019435 A1 | 1/2004 | Winfield et al. |
| 2004/0023295 A1 | 2/2004 | Hamilton et al. |
| 2004/0024293 A1 | 2/2004 | Lawrence et al. |
| 2004/0024543 A1 | 2/2004 | Zhang et al. |
| 2004/0121305 A1* | 6/2004 | Wiegand et al. .................. 435/4 |
| 2006/0134676 A1 | 6/2006 | Kaddurah-Daouk et al. |
| 2006/0134677 A1 | 6/2006 | Kaddurah-Daouk et al. |
| 2006/0134678 A1 | 6/2006 | Kaddurah-Daouk et al. |
| 2007/0026389 A1 | 2/2007 | Kaddurah-Daouk et al. |
| 2007/0072203 A1 | 3/2007 | Kaddurah-Daouk et al. |
| 2007/0172820 A1 | 7/2007 | Kaddurah-Daouk et al. |
| 2007/0172885 A1 | 7/2007 | Kaddurah-Daouk et al. |
| 2007/0178599 A1 | 8/2007 | Kaddurah-Daouk et al. |

FOREIGN PATENT DOCUMENTS

| | | |
|---|---|---|
| WO | WO-86/03006 A1 | 5/1986 |
| WO | WO-92/13273 A1 | 8/1992 |
| WO | WO-93/10802 A1 | 6/1993 |
| WO | WO-93/23075 A1 | 11/1993 |

(Continued)

OTHER PUBLICATIONS

Yasin et al. Melatonin and its analogs inhibit the basal and stimulated release of hypothalamic vasapressin and oxycotin in vitro. Endocrinology, vol. 132, 1993, pp. 1329-1336.*

Metcalfe D. Entrainment of the circadian clock in humans: mechanism and implication for sleep disorders. Impulse: The Premier Journal for Undergraduate Publications in the Neurosciences. Jan. 2004, vol. 1, 11 pages.*

Zhdanova et al. Effects of low oral doses of melatonin, given 2-4 hours before habitual bedtime, on sleep of normal young humans. Sleep, vol. 19, 1996, pp. 423-431.*

Reid et al. Day-time melatonin administration: effects on core temperature and sleep onset latency. Journal of Sleep Research, vol. 5, 1996, pp. 150-154.*

Hardeland et al. Melatonin, a potent agent in antioxidative defense: Actions as a natural food constituent, gastrointestinal factor, drug and prodrug. Nutrition & Metabolism, vol. 2, 2005, p. 22, 15 pages.*

Circadian rhythm. The Hutchinson Unabridged Encyclopedia with Atlas ans Weather Guide, 2009, one page. Retrieved online on May 8, 2011 from <<http://www.credoreference.com/entry/heliconhe/circadian_rhythm>>.*

(Continued)

*Primary Examiner* — Lori A Clow
(74) *Attorney, Agent, or Firm* — McCarter & English, LLP; Elizabeth A. Hanley; Anita M. Bowles

(57) ABSTRACT

Methods for metabolomically determining the biological affects of compounds are described.

102 Claims, 25 Drawing Sheets

(56) References Cited

FOREIGN PATENT DOCUMENTS

| | | |
|---|---|---|
| WO | WO-98/29563 A1 | 7/1998 |
| WO | WO-98/37423 A1 | 8/1998 |
| WO | WO-99/27361 A1 | 6/1999 |
| WO | WO-99/37786 A2 | 7/1999 |
| WO | WO-99/38013 A2 | 7/1999 |
| WO | WO-99/44062 A1 | 9/1999 |
| WO | WO-00/07025 A2 | 2/2000 |
| WO | WO-00/09759 A2 | 2/2000 |
| WO | WO-00/50437 A1 | 8/2000 |
| WO | WO-00/51054 A1 | 8/2000 |
| WO | WO-00/55346 A2 | 9/2000 |
| WO | WO-00/65039 A2 | 11/2000 |
| WO | WO-00/65472 A1 | 11/2000 |
| WO | WO-01/00819 A1 | 1/2001 |
| WO | WO-01/09341 A2 | 2/2001 |
| WO | WO-01/09711 A2 | 2/2001 |
| WO | WO-01/18627 A2 | 3/2001 |
| WO | WO-01/23330 A2 | 4/2001 |
| WO | WO-01/23601 A2 | 4/2001 |
| WO | WO-01/26038 A1 | 4/2001 |
| WO | WO-01/40896 A2 | 6/2001 |
| WO | WO-01/55701 A1 | 8/2001 |
| WO | WO-01/55719 A2 | 8/2001 |
| WO | WO-01/57518 A2 | 8/2001 |
| WO | WO-01/69247 A2 | 9/2001 |
| WO | WO-01/73672 A2 | 10/2001 |
| WO | WO-01/78652 A2 | 10/2001 |
| WO | WO-01/79515 A2 | 10/2001 |
| WO | WO-01/84146 A2 | 11/2001 |
| WO | WO-02/04945 A1 | 1/2002 |
| WO | WO-02/04957 A2 | 1/2002 |
| WO | WO-02/09836 A2 | 2/2002 |
| WO | WO-02/22857 A2 | 3/2002 |
| WO | WO-02/33377 A2 | 4/2002 |
| WO | WO-02/052293 A1 | 7/2002 |
| WO | WO-02/085195 A2 | 10/2002 |
| WO | WO-02/086452 A2 | 10/2002 |
| WO | WO-02/086478 A2 | 10/2002 |
| WO | WO-02/086500 A2 | 10/2002 |
| WO | WO-02/086501 A2 | 10/2002 |
| WO | WO-02/086502 A2 | 10/2002 |
| WO | WO-2004/038381 A2 | 5/2004 |
| WO | WO 2004/111015 A1 * | 12/2004 |
| WO | WO 2005/068611 A1 * | 7/2005 |
| WO | WO-2006/086731 A2 | 8/2006 |

OTHER PUBLICATIONS

Griffin et al. (Nature Reviews: Cancer (2004) vol. 4, pp. 551-561).*
Avery, E.L. et al., "The Use of Lipid Metabolic Profiling to Assess the Biological Impact of Marine Sewage Pollution," *Arch. Environ. Contam. Toxicol.*, vol. 35:229-235 (1998).
Brindle, Joanne T. et al., "Rapid and noninvasive diagnosis of the presence and severity of coronary heart disease using $^1$H-NMR-based metabonomics," *Nature Medicine*, vol. 8(12):1439-1444(2002).
Buchholz, Ame et al., "Metabolomics: quantification of intracellular metabolite dynamics," *Biomolecular Engineering*, vol. 19:5-15 (2002).
Carney, M.W.P. et al., "Red cell folate concentrations in psychiatric patients," *Journal of Affective Disorders*, vol. 19:207-213 (1990).
Gamache, Paul H. et al., "Metabolomic applications of electrochemistry/Mass spectrometry," *Journal of the American Society for Mass Spectrometry*, vol. 15(12):1717-1726 (2004).
Glassbrook, Norm et al., "Metabolic profiling on the right path," *Nature Biotechnology*, vol. 18:1142-1143 (2000).
Hansen, O., "Blood nucleoside and nucleotide studies in mental disease," *Br. J. Psychiatry*, vol. 121(563):341-350 (1972).
Harrington, Michael G. et al., "Differences in Cerebrospinal Fluid Proteins between Patients with Schizophrenia and Normal Persons," *Clinical Chemistry*, vol. 31(5):722-726 (1985).
Holmes, Elaine et al., "Metabonomic Characterization of Genetic Variations in Toxicological and Metabolic Responses Using Probabilistic Neural Networks," *Chem. Res. Toxicol.*, vol. 14:182-191 (2001).
Kell, Douglas B., "Metabolomics and systems biology: making sense of the soup," *Current Opinion in Microbiology*, vol. 7:296-307 (2004).
Matsumoto, I. et al., "A New Chemical Diagnostic Method for Inborn Errors of Metabolism by Mass Spectrometry—Rapid, Practical, and Simultaneous Urinary Metabolites Analysis," *Mass Spectrometry Reviews*, vol. 15:43-57 (1996).
Nicholson, J.K. et al., "'Metabonomics': understanding the metabolic responses of living systems to pathophysiological stimuli via multivariate statistical analysis of biological NMR spectroscopic data," *Xenobiotica*, vol. 29(11):1181-1189 (1999).
Niebroj-Dobosz et al., "Amino acids acting as transmitters in amyotrophic lateral sclerosis (ALS)," *Acta Neurologica Scandinavica*, vol. 100(1):6-11 (1999).
Ning, Cong et al., "Gas chromatographic-mass spectrometric metabolic profiling of patients with fatal infantile myopathy with de Toni-Fanconi-Debré syndrome," Acta Paediatr. Jpn., vol. 38(6):661-666 (1996).
Osher, Susan, "One-Carbon Metabolism in Adults with Major Depression," Thesis, University of Toronto, (1999).
Plumb, Robert S. et al., "Metabonomics: the use of electrospray mass spectrometry coupled to reversed-phase liquid chromatography shows potential for the screening of rat urine in drug development," *Rapid Communications in Mass Spectrometry*, vol. 16:1991-1996 (2002).
Rashed, Mohamed S. et al., "Screening blood spots for inborn errors of metabolism by electrospray tandem mass spectrometry with a microplate batch process and a computer algorithm for automated flagging of abnormal profiles," Clinical Chemistry, vol. 43(7):1129-1141 (1997).
Sauter, Hubert et al., "Metabolic Profiling in Plants, A New Diagnostic Technique," American Chemical Society, Chapter 24 (1991).
Sigma, "Biochemicals, Organic Comopunds and Diagnostic Reagents," Sigma Catalog, p. 253 (1996).
Trethewey, Richard N. et al., "Metabolic profiling: a Rosetta Stone for Genomics?" Current Opinion Plant Biol., vol. 2(2):83-85 (1999).
International Search Report for Application No. PCT/US2007/020213, dated Mar. 7, 2008.

* cited by examiner

Rosiglitazone Maleate (Avandia) in adipocytes

Pathways

| Kegg Pathway (& denotes Super Pathways) | Specific Metabolites changed/pathway (high vs 0 dose, q<0.2) | Specific Metabolites changed/pathway (medium vs 0 dose, q<0.2) | Summary Reference # |
|---|---|---|---|
| Alanine and aspartate metabolism & Selenoamino acid metabolism | Alanine | | 2 |
| | Aspartate | Aspartate | |
| | β-ala | | |
| Aminosugars metabolism | UDP-acetylgalactosamine | | |
| beta-Alanine metabolism | Asp | Asp | 2 |
| | β-ala | | |
| Biosynthesis of steroids & C21-Steroid hormone metabolism & Bile acid biosynthesis & Hedgehog signaling pathway | Chol | Chol | 3 |
| | 3HMG* | | |
| | Gly | | |
| Citrate cycle (TCA cycle) & Reductive carboxylate cycle (CO2 fixation) & Glyoxylate and dicarboxylate metabolism | Malate | Malate | |
| | Succinate | Succinate | |
| | Citrate | | |
| Cyanoamino acid metabolism & Cysteine metabolism & Sphingolipid metabolism & Methane metabolism | Gly | | 2 |
| | Ser | | |
| Fructose and mannose metabolism | G6P | G6P | 5 |
| Galactose metabolism | Glycerol | Glycerol | |
| | Lactose | Lactose | |
| Glutamate metabolism & D-Glutamine and D-glutamate metabolism | Succinate | Succinate | 2 |
| | Phe | Phe | |
| | Gln | | |
| | Tyr | | |
| | γ-glu-cys | | |
| | γ-Glu-gln* | | |
| | 5-oxopro | 5-oxopro | |

Interpretation 5-oxoproline is generated via oxoprolinase (rate-limiting) in the g-glutamyl cycle1. Increased 5-oxoproline resulted from increased g-glu-cys, due to low activity of glutathione synthase. Decreased g-glutamy cycle activity could limit transport of AA against a gradient, affecting AA levels 2. Increases in various AA is also likely related to increased protein turn over. Consistent with increased generation of AA, urea cycle intermdiates and polyamines were increased 3. Typically, rosiglitazone increases cholesterol in cultured adipocytes by increasing uptake of cholesterol from media via activation of scavenger receptors (e.g., oxidized LDL receptor 1). Cholesterol decreased, and this could be related to a lack of cholesterol provided in the media3. The decrease in glycerol is consistent with rosiglitazone-induced increases in glycerol kinase 4. Typically, rosiglitazone increases free fatty acids (FFA) in adipocytes, and these FFA are rapidly stored as triacylglycerols (TAG). Our current system does not detect intact TAG. The increase in G6P, and decrease in 6-phosphogluconate and ribulose 5-P, suggests decreased flux through the pentose phosphate pathway.

Fig. 4

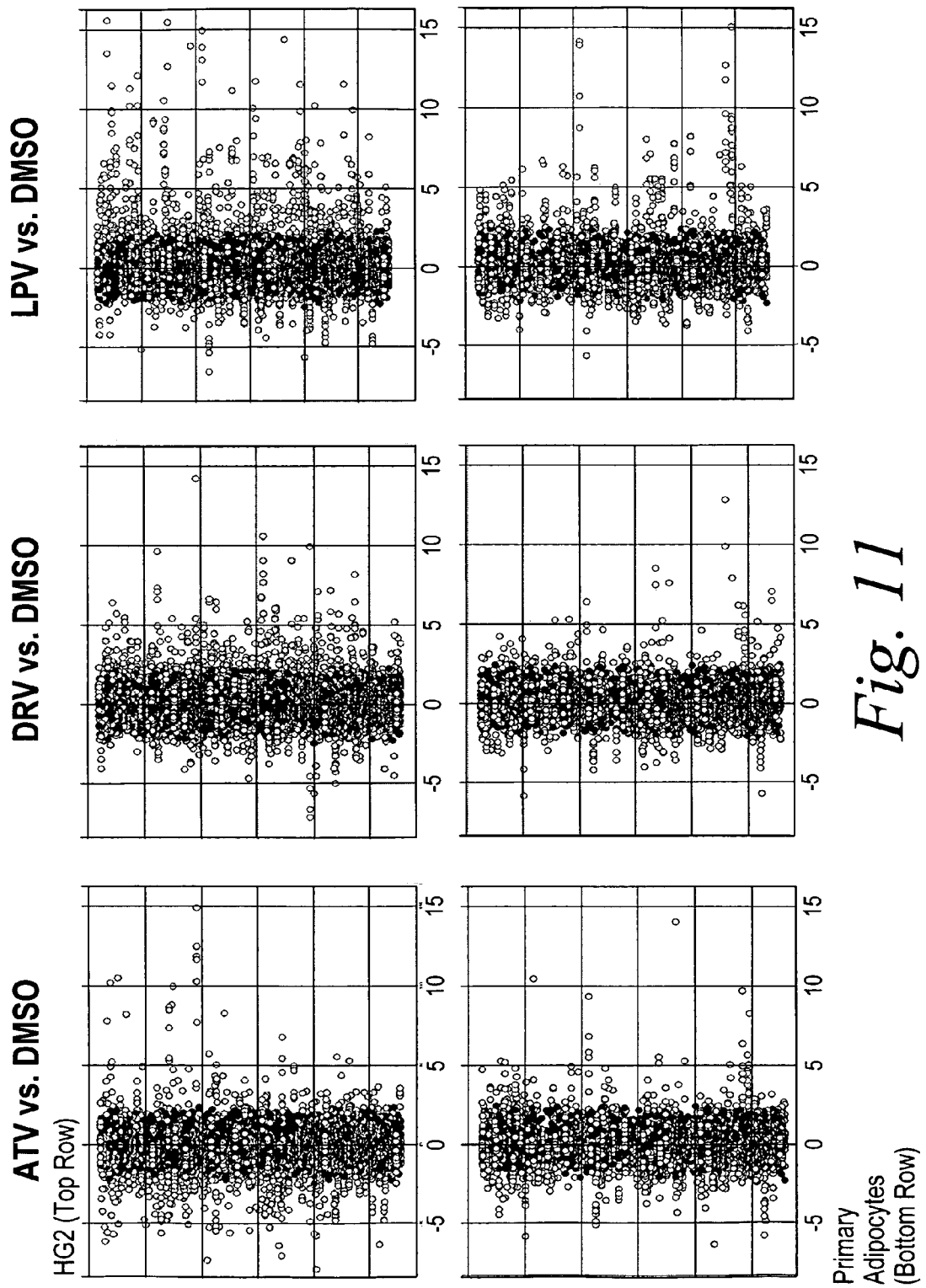

| KEGG Super Pathway | Pathway (KEGG) | KEGG | Name (KEGG) | Name (Metabolon) | Hepatocytes ATV | Hepatocytes DRV | Hepatocytes LPV | Primary Adipocytes ATV | Primary Adipocytes DRV | Primary Adipocytes LPV |
|---|---|---|---|---|---|---|---|---|---|---|
| Amino Acid Metabolism | Alanine and aspartate metabolism | C00099 | beta-Alanine | beta-alanine | | | 2.24 | | | 1.65 |
| | | C00122 | Fumarate | fumaric acid | | | | 0.83 | | 0.79 |
| | | C00152 | L-Asparagine | asparagine | | | 3.80 | | | 1.17 |
| | | C03406 | N-(L-Arginino)succinate | arginino-succinate | | 0.55 | | 1.80 | | |
| | | C00049 | L-Aspartate | aspartate | 0.72 | | | 1.22 | | 1.33 |
| | | C02571 | O-Acetylcarnitine | O-acetyl-L-carnitine-hydrochloride | | 1.66 | | | | |
| | | C00025 | L-Glutamate | glutamic acid | 0.84 | | 1.30 | | | |
| | | C00134 | Putrescine | Putrescine | 4.92 | 2.40 | 22.00 | 1.68 | | 4.18 |
| | | C00170 | 5'-Methylthioadenosine | 5-s-methyl-5-thioadenosine | 0.74 | | 0.86 | | | 1.36 |
| | | C00122 | Fumarate | fumaric acid | | | | 0.83 | | 0.79 |
| | Arginine and proline metabolism | C00086 | Urea | urea | 0.79 | 1.31 | | 1.28 | | 1.63 |
| | | C00148 | L-Proline | proline | | | 1.66 | 0.77 | | 0.78 |
| | | C00327 | L-Citrulline | N-5-aminocarbonyl-L-ornithine | | 0.55 | | 1.80 | | |
| | | C03406 | N-(L-Arginino)succinate | arginino-succinate | | | | | | |
| | | C00035 | 4-Guanidinobutanoate | 4-Guanidinobutanoic acid | 0.78 | | 0.83 | | | |
| | | C00019 | S-Adenosyl-L-methionine | S-5-adenosyl-L-methionine | | 1.40 | 1.20 | | | |
| | | C00049 | L-Aspartate | aspartate | 0.72 | | | | | |
| | | C00025 | L-Glutamate | glutamic acid | 0.84 | | 1.30 | | | |
| | Urea cycle and metabolism of amino groups | C00134 | Putrescine | Putrescine | 4.92 | 2.40 | 22.00 | 1.68 | | 4.18 |
| | | C00122 | Fumarate | fumaric acid | | | | 0.83 | | 0.79 |
| | | C00086 | Urea | urea | 0.79 | 1.31 | | 1.28 | | 1.63 |
| | | C00148 | L-Proline | proline | | | 1.66 | 0.77 | | 0.78 |
| | | C00327 | L-Citrulline | N-5-aminocarbonyl-L-ornithine | | 0.55 | | 1.80 | | |
| | | C03406 | N-(L-Arginino)succinate | arginino-succinate | | | | | | |
| | | C00049 | L-Aspartate | aspartate | 0.72 | | | | | |

Fig. 12A Continued

| KEGG Super Pathway | Pathway (KEGG) | KEGG | Name (KEGG) | Name (Metabolon) | Hepatocytes ATV | Hepatocytes DRV | Hepatocytes LPV | Primary Adipocytes ATV | Primary Adipocytes DRV | Primary Adipocytes LPV |
|---|---|---|---|---|---|---|---|---|---|---|
| Amino Acid Metabolism | Glutamate metabolism | C00064 | L-Glutamine | glutamine | | | 4.44 | 1.39 | | 1.64 |
| | | C00025 | L-Glutamate | glutamic acid | 0.84 | | 1.30 | | | |
| | | C00026 | 2-Oxoglutarate | alpha-keto-glutarate | 2.88 | | 2.21 | 1.90 | | 1.54 |
| | | C00669 | gamma-L-Glutamyl-L-cysteine | gamma-L-Glutamyl-L-cysteine | | | 1.80 | | | |
| | | C00051 | Glutathione | glutathione-reduced | 0.13 | 0.19 | 2.88 | 0.91 | 0.84 | 0.90 |
| | | C00127 | Oxidized glutathione | ** oxidized-glutathione | | | 3.36 | 0.80 | | |
| | | NA | NA | Isobar-32-includes-N-acetyl-D-glucosamine-N-acetyl-D-mannosamine | 0.57 | | | | | |
| | | C00357 | N-Acetyl-D-glucosamine 6-phosphate | N-acetylglucosamine-6-sulfate | | 0.80 | 1.40 | | | 1.37 |
| | Glycine, serine and threonine metabolism | C01005 | O-Phospho-L-serine | 3-phospho-l-serine | | | 2.16 | 1.18 | | |
| | | C00188 | L-Threonine | threonine | 1.64 | | 1.24 | 0.19 | 0.42 | 0.14 |
| | | C00197 | 3-Phospho-D-glycerate | 3-phospho-d-glycerate | | | 1.41 | | | |
| | | C00065 | L-Serine | l-serine | 0.79 | | 1.52 | | | 1.63 |
| | | C00037 | Glycine | glycine | | | 1.52 | 1.69 | | 1.84 |
| | | NA | NA | homoserine | 0.84 | | 1.30 | | | |
| | Histidine metabolism | C00025 | L-Glutamate | glutamic acid | 0.79 | | 2.53 | | | |
| | | C00135 | L-Histidine | histidine | | 1.52 | | | | |
| | | C00388 | 1H-Imidazole-4-ethanamine | histamine | 0.72 | | 1.52 | | | |
| | | C00049 | L-Aspartate | aspartate | | | 1.41 | | | |
| | Lysine biosynthesis | C00956 | L-2-Aminoadipate | alpha-amino-adipate | 0.79 | | 1.35 | | | 1.30 |
| | Cysteine metabolism | C00037 | Glycine | glycine | | | 1.41 | | | 1.63 |
| | Methionine metabolism | C00065 | L-Serine | l-serine | | | | | | |
| | | C00073 | L-Methionine | methionine | | | 1.41 | | | 1.14 |
| | | C00065 | L-Serine | l-serine | | | | | | |
| | Methionine metabolism | C00019 | S-Adenosyl-L-methionine | S-5-adenosyl-l-methionine | | 1.40 | 1.20 | | | |

Fig. 12A Continued

| KEGG Super Pathway | Pathway (KEGG) | KEGG | Name (KEGG) | Name (Metabolon) | Hepatocytes | | | Primary Adipocytes | | |
|---|---|---|---|---|---|---|---|---|---|---|
| | | | | | ATV | DRV | LPV | ATV | DRV | LPV |
| Amino Acid Metabolism Continued | Phenylalanine metabolism | C00079 | L-Phenylalanine | phenylalanine | | | 1.40 | | | 1.53 |
| | tryptophan biosysthesis | C01179 | 3-(4-Hydroxyphenyl)pyruvate | 4-hydroxyphenylpyruvate | | | 6.95 | 1.49 | | |
| | Tryptophan metabolism | C00078 | L-Tryptophan | tryptophan | | | 1.88 | | | |
| | | C00328 | L-Kynurenine | L-kynurenine | | | 1.38 | | | |
| | | C01717 | 4-Hydroxy-2-quinolinecarboxylic | kynurenic acid | | | | 0.77 | | 0.78 |
| | | C00026 | 2-Oxoglutarate | alpha-keto-glutarate | 2.88 | | 2.21 | 1.90 | | 1.54 |
| | Tyrosine metabolism | C00082 | L-Tyrosine | tyrosine | | | 1.70 | 0.92 | | 1.07 |
| | | C01179 | 3-(4-Hydroxyphenyl)pyruvate | 4-hydroxyphenylpyruvate | | | 6.95 | 1.49 | | 1.53 |
| | | C00122 | Fumarate | fumaric acid | | | | 0.83 | | 0.79 |
| | Valine, leucine and isoleucine degradation | C00123 | L-Leucine | leucine | | | 1.52 | 0.91 | | |
| | | C00407 | L-Isoleunine | isoleunine | | | 2.07 | 0.85 | | |
| | | C00183 | L-Valine | valine | | | 1.61 | 0.86 | | 0.92 |
| | | C00041 | 3-Methyl-2-oxobutanoic acid | 3-methyl-2-oxobutyriate | | 1.52 | 0.73 | | | |

Fig. 12B

| KEGG Super Pathway | Pathway (KEGG) | KEGG | Name (KEGG) | Name (Metabolon) | Hepatocytes ATV | Hepatocytes DRV | Hepatocytes LPV | Primary Adipocytes ATV | Primary Adipocytes DRV | Primary Adipocytes LPV |
|---|---|---|---|---|---|---|---|---|---|---|
| Carbohydrate Metabolism | Aminosugars metabolism | C00270 | N-Acetylneuraminate | N-acetylneuraminate | 0.57 | | | 1.77 | | |
| | | NA | NA | Isobar-32-includes-N-acetyl-D-glucosamine-N-a | | | 1.40 | | | |
| | | C00357 | N-Acetyl-D-glucosamine 6-phosphate | N-acetylglucosamine-6-sulfate | | | 1.30 | | | |
| | Butanoate metabolism | C00025 | L-Glutamate | glutamic acid | 0.84 | | | | | |
| | | C00026 | 2-Oxoglutarate | alpha-keto-glutarate | 2.88 | | 2.21 | 1.90 | | 1.54 |
| | | C00026 | 2-Oxoglutarate | alpha-keto-glutarate | 2.88 | | 2.21 | 1.90 | | 1.54 |
| | Citrate cycle (TCA cycle) | C00074 | Phosphoenolpyruvate | phosphoenolpyruvate | | | | 0.45 | 0.55 | 0.29 |
| | | C00149 | (S)-Malate | malic acid | | | | 0.88 | 0.81 | 0.80 |
| | | C00158 | Citrate | citric acid | | 1.83 | 1.58 | | | |
| | | C00122 | Fumarate | fumaric acid | | | | 0.83 | | 0.79 |
| | Pyruvate metabolism | C00186 | (S)-Lactate | lactate | | | | 0.85 | | 0.78 |
| | | C00074 | Phosphoenolpyruvate | phosphoenolpyruvate | | | | 0.45 | 0.55 | 0.29 |
| | | C00149 | (S)-Malate | malic acid | | | | 0.88 | | 0.80 |
| | Fructose and mannose metabolism | C00159 | D-mannose | D-mannose | | | 1.32 | 1.39 | | 1.44 |
| | | C00275 | D-Mannose 6-phosphate | mannose-6-phosphate | | 1.59 | 1.53 | 2.77 | 2.25 | 2.76 |
| | | C05345 | beta-D-Fructose 6-phosphate | beta-D-fructose-6-phosphate | | | | 0.56 | 0.74 | 0.54 |
| | | C00794 | D-Sorbitol | sorbitol | | | | 0.36 | 0.57 | 0.32 |
| | | C00577 | D-Glyceraldehyde | glyceraldehyde | | | 1.76 | 2.13 | 1.77 | 1.82 |
| | | C01094 | D-Fructose 1-phosphate | Isobar-18-includes-D-fructose-1-phosphate-bet | | 1.71 | 1.30 | 0.32 | | 0.43 |
| | | C00096 | GDP-mannose | guanosine-5-diphospho-D-mannose- | | 1.68 | | 0.59 | | 0.57 |
| | | C00267 | alpha-D-glucose | D-glucose | | 0.81 | 1.53 | 1.39 | | 1.44 |
| | Galactose metabolism | C00243 | Lactose | beta-D-lactose | | 1.59 | 1.53 | 0.56 | 0.74 | 0.54 |
| | | C00159 | D-mannose | mannose | | 1.15 | | | | |
| | | C00794 | D-Sorbitol | sorbitol | 0.83 | | | | | |
| | | C00137 | myo-Inositol | inositol | | 1.71 | 1.30 | 0.32 | | 0.43 |
| | | C00267 | alpha-D-glucose | D-glucose | | | | | | |

Fig. 12C Continued

| KEGG Super Pathway | Pathway (KEGG) | KEGG | Name (KEGG) | Name (Metabolon) | Hepatocytes ATV | Hepatocytes DRV | Hepatocytes LPV | Primary Adipocytes ATV | Primary Adipocytes DRV | Primary Adipocytes LPV |
|---|---|---|---|---|---|---|---|---|---|---|
| Carbohydrate Metabolism | Glycolysis / Gluconeogenesis | C00186 | (S)-Lactate | lactate | | | | 0.85 | 0.81 | 0.78 |
| | | C00074 | Phosphoenolpyruvate | phosphoenolpyruvate | | | | 0.45 | 0.55 | 0.29 |
| | | C00197 | 3-Phospho-D-glycerate | 3-phospho-d-glycerate | 1.64 | | | 0.19 | 0.42 | 0.14 |
| | | C05345 | beta-D-Fructose 6-phosphate | beta-D-fructose-6-phosphate | | 1.71 | | 2.77 | 2.25 | 2.76 |
| | | C00267 | alpha-D-glucose | D-glucose | | | 1.30 | 0.32 | | 0.43 |
| | metabolism | C00258 | D-Glycerate | glycerate | | 0.47 | | | | 0.63 |
| | Inositol phosphate metabolism | C01177 | Inositol 1-phosphate | inositol-1-phosphate | | | 1.24 | 0.79 | | |
| | Pentose phosphate pathway | C00199 | D-Ribulose 5-phosphate | D-Ribulose 5-phosphate | | 0.80 | | | | |
| | | C05345 | beta-D-Fructose 6-phosphate | beta-D-fructose-6-phosphate | | | | 2.77 | 2.25 | 2.76 |
| | | C00345 | 6-Phospho-D-gluconate | 6-phosphogluconic acid (6-Phospho-D-gluconate) | | 0.73 | 1.67 | 0.63 | 0.65 | 0.67 |
| | | C00198 | D-Glucono-1,5-lactone | glucono-gamma-lactone | | 1.68 | | 0.67 | | 0.48 |
| | | C00267 | alpha-D-glucose | D-glucose | | 1.71 | 1.30 | 0.32 | | 0.43 |
| | Propanoate metabolism | C00099 | beta-Alanine | beta-alanine | | | 2.24 | | | 1.65 |
| | Starch and sucrose metabolism | C05345 | beta-D-Fructose 6-phosphate | beta-D-fructose-6-phosphate | | | | 2.77 | 2.25 | 2.76 |
| | | C00208 | Maltose | maltose | | 1.68 | 1.24 | 0.58 | | 0.57 |
| | | C00267 | alpha-D-glucose | D-glucose | | 1.71 | 1.30 | 0.32 | | 0.43 |
| Energy Metabolism | Oxidative phosphorylation | C00008 | ADP | adenosine-5-diphosphate | | | 4.88 | | | |
| | | C00122 | Fumarate | fumaric acid | | | | 0.83 | | 0.79 |
| | | C00009 | Orthophosphate | phosphate | | | | 0.68 | 0.82 | 0.73 |
| | Reductive carboxylate cycle (CO2 fixation) | C00197 | 3-Phospho-D-glycerate | 3-phospho-d-glycerate | 1.64 | | | 0.19 | 0.42 | 0.14 |
| | | C00199 | D-Ribulose 5-phosphate | D-Ribulose 5-phosphate | | 0.80 | | | | |
| | | C00049 | L-Aspartate | aspartate | 0.72 | | | | | |
| | | C00122 | Fumarate | fumaric acid | | | | 0.83 | | 0.79 |

Fig. 12C Continued

| KEGG Super Pathway | Pathway (KEGG) | KEGG | Name (KEGG) | Name (Metabolon) | Hepatocytes ATV | Hepatocytes DRV | Hepatocytes LPV | Primary Adipocytes ATV | Primary Adipocytes DRV | Primary Adipocytes LPV |
|---|---|---|---|---|---|---|---|---|---|---|
| Lipid Metabolism | Bile acid biosynthesis | C00041 | L-Alanine | alanine | | 1.51 | 1.52 | | | 1.63 |
| | | C00245 | Taurine | taurine | | | 1.52 | | | 1.45 |
| | | C00037 | Glycine | glycine | 0.79 | | | 1.71 | 1.41 | 1.16 |
| | Fatty acid metabolism | C06424 | Tetradecanoic acid | tetradecanoate | | | | | | |
| | | C00249 | Hexadecanoic acid | n-hexadecanoic acid | | | | 1.30 | | |
| | | C01530 | Octadecanoic acid | octadecanoate | 0.88 | | | | | |
| | | C08362 | (9Z)-Hexadecenoic acid | palmitoleate (16:1n7) | | | | 1.81 | 1.42 | 1.50 |
| | | C00712 | (9Z)-Octadecenoic acid | oleic acid (18:1n9) | | | | 1.37 | | 1.21 |
| | | | | 16:1n7/16:0 | | | | 1.40 | | 1.29 |
| | | | | 18:1n9/18:0 | | | | | | |
| | | C02571 | O-Acetylcarnitine | O-acetyl-L-carnitine-hydrochloride | | 1.66 | | 1.22 | | 1.33 |
| | | C00258 | D-Glycerate | glycerate | | 0.47 | | | | 0.63 |
| | Glycerolipid metabolism | C00093 | sn-Glycerol 3-phosphate | sn-Glycerol-3-phosphate | 0.81 | | 0.83 | 0.41 | 0.55 | 0.33 |
| | | C00577 | D-Glyceraldehyde | glyceraldehyde | | 0.82 | 0.88 | 0.36 | 0.57 | 0.32 |
| | | C01885 | 1-Acylglycerol | monopalmitin | | | | | | |
| | | C01885 | 1-Acylglycerol | 1-stearoyl-rac-glycerol | 0.76 | | 3.26 | 1.82 | 1.36 | 3.53 |
| | Glycerophospholipid metabolism | C00346 | Ethanolamine phosphate | o-phosphoethanolamine | | | | | | |
| | | C00093 | sn-Glycerol 3-phosphate | sn-Glycerol-3-phosphate | 0.81 | | 0.83 | 0.41 | 0.55 | 0.33 |
| | | C00670 | sn-glycero-3-Phosphocholine | L-alpha-glycerophosphorylcholine | 0.54 | 0.54 | 0.33 | | | 0.29 |
| | Sphingolipid metabolism | C00065 | L-Serine | L-serine | | 1.41 | | | | |
| | | C00346 | Ethanolamine phosphate | o-phosphoethanolamine | | | 3.26 | 1.82 | 1.36 | 3.53 |
| | | C00319 | Sphingosine | D-sphingosine | | | | | 1.38 | |

Fig. 12D Continued

| KEGG Super Pathway | Pathway (KEGG) | KEGG | Name (KEGG) | Name (Metabolon) | Hepatocytes ||| Primary Adipocytes |||
|---|---|---|---|---|---|---|---|---|---|---|
| | | | | | ATV | DRV | LPV | ATV | DRV | LPV |
| Metabolism of Cofactors and Vitamins | Folate biosynthesis | C00504 | Folate | folic acid | | | 1.39 | 0.44 | | 0.66 |
| | One carbon pool by folate | C00504 | Folate | folic acid | | | 1.39 | 0.44 | | 0.66 |
| | Pantothenate and CoA biosynthesis | C00099 | beta-Alanine | beta-alanine | | | 2.24 | | | 1.65 |
| | | C00864 | Pantothenate | pantothenic acid | 2.11 | 1.35 | 4.17 | 1.22 | | 1.43 |
| | | C00183 | L-Valine | valine | | | 1.61 | 0.86 | | 0.92 |
| | | C00141 | 3-Methyl-2-oxobutanoic acid | 3-methyl-2-oxobutyriate | | 1.52 | 0.73 | | | |
| | Porphyrin and chlorophyll metabolism | C00025 | L-Glutamate | glutamic acid | 0.84 | | 1.30 | | | 0.70 |
| | Riboflavin metabolism | C00255 | Riboflavin | riboflavine | | 1.20 | | 0.74 | | |
| | Thiamine metabolism | C00378 | Thiamin | thiamine | 0.61 | | 0.75 | | | 0.65 |
| | Thiamine metabolism | C00081 | Thiamin monophosphate | thiamin-monophosphate | 0.66 | | 0.74 | 1.59 | | 2.61 |
| | Vitamin B6 metabolism | C00314 | Pyridoxine | vitamin-B6 | | 1.36 | 1.23 | 0.65 | | 0.68 |
| | | C00534 | Pyridoxamine | pyridoxamine | | 1.57 | 1.38 | | | |

Fig. 12D Continued

| KEGG Super Pathway | Pathway (KEGG) | KEGG | Name (KEGG) | Name (Metabolon) | Hepatocytes | | | Primary Adipocytes | | |
|---|---|---|---|---|---|---|---|---|---|---|
| | | | | | ATV | DRV | LPV | ATV | DRV | LPV |
| Metabolism of Other Amino Acids | beta-Alanine metabolism | C00099 | beta-Alanine | beta-alanine | | | 2.24 | | | 1.65 |
| | D-Glutamine and D-glutamate metabolism | C00049 | L-Aspartate | aspartate | 0.72 | | | | | |
| | | C00064 | L-Glutamine | glutamine | | | 4.44 | 1.39 | | 1.64 |
| | | C00025 | L-Glutamate | glutamic acid | 0.84 | | 1.30 | | | |
| | | C00026 | 2-Oxoglutarate | alpha-keto-glutarate | 2.88 | | 2.21 | 1.90 | | 1.54 |
| | Glutathione metabolism | C00025 | L-Glutamate | glutamic acid | 0.84 | | 1.30 | | | |
| | | C00051 | Glutathione | glutathione-reduced | 0.13 | 0.19 | 2.88 | 0.91 | | 0.90 |
| | | C00127 | Oxidized glutathione | ** oxidized-glutathione | | | 3.36 | 0.80 | | |
| | | C00669 | gamma-L-Glutamyl-L-cysteine | gamma-L-Glutamyl-L-cysteine | | | 1.80 | | | |
| | | C01879 | 5-Oxoproline | 5-oxoproline | 0.74 | | 1.38 | 0.69 | | 0.80 |
| | | NA | NA | X-1595-possible-glutathione-metabolite | | | 1.40 | 1.18 | | 2.02 |
| | | C00037 | Glycine | glycine | 0.79 | | 1.52 | | | 1.63 |
| | Cyanoamino acid metabolism | C00065 | L-Serine | L-serine | | | 1.41 | | | |
| | | C00037 | Glycine | glycine | 0.79 | | 1.52 | | | |
| | Taurine and hypotaurine metabolism | C00245 | Taurine | taurine | | 1.51 | | | 0.84 | 1.63 |
| | Selenoamino acid metabolism | C00041 | L-Alanine | alanine | | | 1.52 | | | |

*Fig. 12D* Contunued

| KEGG Super Pathway | Pathway (KEGG) | KEGG | Name (KEGG) | Name (Metabolon) | Hepatocytes ATV | Hepatocytes DRV | Hepatocytes LPV | Primary Adipocytes ATV | Primary Adipocytes DRV | Primary Adipocytes LPV |
|---|---|---|---|---|---|---|---|---|---|---|
| Nucleotide Metabolism | Purine metabolism | C00064 | L-Glutamine | glutamine | | | 4.44 | 1.39 | | 1.64 |
| | | C00147 | Adenine | adenine | 0.85 | | | 1.34 | | |
| | | C00294 | Inosine | inosine | | | 1.40 | | | |
| | | C00330 | Deoxyguanosine | 2'-deoxyguanosine | | | | 1.48 | 1.53 | 1.65 |
| | | C00387 | Guanosine | guanosine | | 0.80 | 0.82 | | | |
| | | C00086 | Urea | urea | 0.79 | 1.31 | | | | |
| | | C00020 | AMP | adenosine-5-monophosphate | 0.82 | | 1.10 | 0.62 | | 0.73 |
| | | C00008 | ADP | adenosine-5-diphosphate | | | 4.88 | | | |
| | | C00385 | Xanthine | xanthine | | 0.84 | 0.83 | | | |
| | | C01762 | Xanthosine | xanthosine | | 0.73 | 0.77 | | | |
| | | C04083 | N6-(delta2-Isopentenyl)-adenine | 6-gamma-gamma-dimethylallyl-amino-purine | 0.46 | 0.61 | 0.79 | | | |
| | Pyrimidine metabolism | C00064 | L-Glutamine | glutamine | | | 4.44 | 1.39 | | 1.64 |
| | | C00099 | beta-Alanine | beta-alanine | | | 2.24 | | | 1.65 |
| | | C00178 | Thymine | thymine | | | | 0.77 | | 0.87 |
| | | C00299 | Uridine | uridine | | 0.77 | 0.72 | | | |
| | | C00526 | Deoxyuridine | 2-deoxyuridine | | | | | 1.22 | |
| | | C00055 | CMP | cytidine 5'-monophosphate | | | 1.24 | 1.52 | | 1.61 |
| | Phosphatidylinositol signaling system | C01177 | Inositol 1-phosphate | inositol-1-phosphate | | | | 0.79 | | |
| Signaling Molecules & Interaction | Neuroactive ligand-receptor interaction | C00099 | beta-Alanine | beta-alanine | | | 2.24 | | | 1.65 |
| | | C00245 | Taurine | taurine | | 1.51 | | | | |
| | | C00008 | ADP | adenosine-5-diphosphate | | | 4.88 | | | |
| | | C00037 | Glycine | glycine-1 | 0.79 | | 1.52 | | | 1.63 |

*Fig. 12E*

| KEGG Super Pathway | Pathway (KEGG) | KEGG | Name (KEGG) | Name (Metabolon) | Hepatocytes | | | Primary Adipocytes | | |
|---|---|---|---|---|---|---|---|---|---|---|
| | | | | | ATV | DRV | LPV | ATV | DRV | LPV |
| | | C00489 | glutarate | glutarate | | 1.39 | 1.23 | | | |
| | | C03761 | NA | 3-hydroxy-3-methylglutarate | 1.26 | 1.35 | 1.43 | | | |
| | | C00257 | D-Gluconic acid | gluconic acid | 0.66 | | 0.73 | | | 0.64 |
| | | NA | NA | heptadecanoic acid | 0.83 | 0.83 | 0.86 | | | |
| | | C03672 | NA | (p-hydroxyphenyl)lactate | 2.33 | 1.64 | 9.12 | 1.65 | | 1.52 |
| | | NA | NA | bestatin | | 1.59 | 1.30 | 0.54 | | 0.59 |
| | | C05283 | NA | gamma-L-glutamyl-L-glutamine | 0.20 | 0.50 | 2.85 | | | |
| | | NA | NA | p-cresol-sulfate** | 0.74 | | | 0.62 | | 0.64 |
| | | NA | NA | phenylacetylglutamine-or-formyl-N-acetyl-5-methoxykynurenamine** | 0.68 | | 0.82 | | | |
| | | NA | NA | picolinamide-or-Isonicotinamide** | | | | 0.71 | | 0.69 |
| | | C00014 | NA | n-acetyl-l-aspartate | | | | 0.84 | 0.74 | 0.71 |
| | | NA | NA | **hydroxyproline-form-of-bradykinin | | | | 0.43 | | 0.52 |
| N/A | NA | NA | NA | Isobar-1-includes-mannose-fructose-glucose-galactose-alpha-L-sorbopyranose-Inositol-D-allose | | 1.65 | 1.19 | 0.71 | | 0.72 |
| | | NA | NA | Isobar-3-includes-inositol-1-phosphate-mannose-6-phosphate-glucose-6-phosphate-D-mannose-1-phosphate-alpha-D-glucose-1-phosphate-alpha-D-galactose-1-phosphate | | | | 1.60 | | 1.48 |
| | | NA | NA | Isobar-4-includes-Gluconic acid-DL-arabinose-D-ribose-L-xylose-DL-lyxose | | 0.74 | 0.87 | 1.28 | | 1.15 |
| | | C02301 | NA | DL-hexanoyl-carnitine | | 1.19 | 3.08 | 1.46 | | 1.53 |
| | | NA | NA | X-3183-possible-gamma-L-glutamyl-L-phenylalanine-or-aspartame | 1.29 | 1.57 | 1.85 | | | |
| | | C00860 | NA | L-histidinol | 1.41 | 1.68 | 2.22 | | | |
| | | C05994 | NA | 2-isopropylmalate | | 1.38 | 1.30 | 0.75 | | 0.79 |
| | | NA | NA | 2-methylhippuric acid | | 1.96 | | | | |
| | | C00587 | NA | 3-hydroxybenzoate | 1.62 | | 2.45 | 0.80 | 0.72 | 0.86 |
| | | C05568 | NA | L-beta-imidazolelactate | | | | | | |
| | | NA | NA | ethylmalonic acid | 1.40 | 1.25 | | 1.59 | 0.74 | 0.83 |
| | | NA | NA | thiamin-monophosphate | 0.66 | | 0.74 | | | 2.61 |

*Fig. 12F* Continued

| KEGG Super Pathway | Pathway (KEGG) | KEGG | Name (KEGG) | Name (Metabolon) | Hepatocytes ATV | Hepatocytes DRV | Hepatocytes LPV | Primary Adipocytes ATV | Primary Adipocytes DRV | Primary Adipocytes LPV |
|---|---|---|---|---|---|---|---|---|---|---|
| N/A | NA | C00383 | NA | malonate | | | | | | 1.99 |
| | | C02976 | NA | D-fructose-1-phosphate | 0.72 | | 1.10 | | | |
| | | C00050 | NA | uridine-diphosphate-N-acetylmuraminate | 1.88 | 1.46 | 3.06 | 1.77 | 1.67 | 2.08 |
| | | NA | NA | X-4030-possible-glutethimide-or-securinine | 0.61 | 0.73 | | | | |
| | | NA | NA | X-4091-possible-gamma-glutamyl-glutamic acid | 0.67 | 1.61 | 2.76 | | | |
| | | NA | NA | X-4096-gamma-glu-gly-leu- | | 0.74 | 0.64 | | | |
| | | C12143 | NA | Isobar-22-includes-glutamic acid-O-acetyl-l-serine | 0.81 | 0.78 | | 1.56 | | 1.67 |
| | | C03045 | NA | Isobar-17-includes-arginine-N-alpha-acetyl-ornithine | | | 0.79 | 1.24 | | 1.19 |
| | | NA | NA | Isobar-33-includes-uridine-5-diphosphogalactose-uridine-5-diphosphoglucose | 0.68 | | | | | |
| | | C12143 | NA | 2-aminoacridone | | 0.78 | 0.78 | | | |
| | | C03045 | NA | DL-alpha-hydroxystearate | | | | 0.68 | | 0.70 |
| | | NA | NA | 4-acetominophen-sulfate | 1.60 | | | | | |
| | | C00310 | NA | D-xylulose | | 0.78 | | | | |
| | | NA | NA | cys-gly-oxidized-acetate | 0.85 | 1.50 | 2.35 | | | 1.55 |
| | | C01732 | NA | gamma-glu-leu | | 1.26 | 1.35 | | | |
| | | C00680 | NA | mesaconate | | 1.29 | | | | |
| | | C06772 | NA | diaminopimelate | 0.20 | 0.49 | 0.41 | | | |
| | | NA | NA | diethanolamine | 0.58 | | | | | |
| | | C00209 | NA | trans-b-hydromuconate | | | 2.11 | 1.76 | | 2.78 |
| | | NA | NA | oxalate | | 1.28 | 1.30 | 1.26 | | 1.18 |
| | | C00503 | NA | meso-erythritol | | 1.16 | 1.26 | 0.72 | | 0.70 |
| | | NA | NA | 2-2-dimethylsuccinate | | | | | | |
| | | C02037 | NA | gly-gly | | | 1.58 | 0.79 | | |
| | | C01933 | NA | L-norleucine | | | | 1.34 | | |
| | | NA | NA | isopropyl-beta-D-l-thiogalactopyranoside | | | | | | 1.19 |

Fig. 12F Continued

| KEGG Super Pathway | Pathway (KEGG) | KEGG | Name (KEGG) | Name (Metabolon) | Hepatocytes | | | Primary Adipocytes | | |
|---|---|---|---|---|---|---|---|---|---|---|
| | | | | | ATV | DRV | LPV | ATV | DRV | LPV |
| N/A Continued | NA | NA | NA | 1-6-anhydro-beta-d-glucose | | 2.58 | | | | |
| | | NA | NA | 5-sulfosalicylate | 0.89 | | 1.83 | 0.82 | | 0.86 |
| | | NA | NA | Isobar-49-includes-cysteine-trizma-acetate | 0.73 | 0.63 | | 1.31 | | 1.19 |
| | | NA | NA | Isobar-52-includes-iminodiacetate-L-aspartate | | | | 1.82 | | |
| | | NA | NA | Isobar-54-includes-terephthalate-isophthalate | | 1.34 | | | | |
| | | NA | NA | glycyl-sarcosine | | | 0.74 | | | |
| | | NA | NA | l-aspartyl-l-phenylalanine | | 0.62 | 0.55 | | | |
| Glycan Biosynthesis & Metabolism | N-Glycan biosynthesis | C00096 | GDP-mannose | guanosine-5-diphospho-D-mannose- | | | 1.76 | | | |
| Xenobiotics Biodeg. & Metabolism | Benzoate degradation via hydroxylation | C00633 | 4-Hydroxybenzaldehyde | p-hydroxybenzaldehyde | | | | 0.80 | | |
| Biosynthesis of Secondary Metabolites | Alkaloid biosynthesis II | C01672 | Cadaverine | 1-5-diaminopentane | 2.01 | 1.71 | 3.14 | | | |
| | | | | Relative metabolite level: Treated/Control | | | | | | |

*Fig. 12G*

| SUMMARY (Pathway-centric) | |
|---|---|
| Primary Pathway Name | Summary: |
| Arginine and proline metabolism | Increase in the polyamine putrescine, particularly with LPV in hepatocytes, may relate to up regulated ODC, and affect cell signaling and proliferation. 5'-Methylthioadenosine (MTA) may be a marker for putrescine degradation, as it is formed via conversion of putrescine to spermidine; and spermidine to spermine. |
| Glutamate metabolism | 2-Oxoglutarate ( KG) is utilized in nitrogen metabolism reactions, but also to support glyceroneogenesis via conversion to G3P via ALT, PC and PEPCK. |
| Tryptophan metabolism | L-Tryptophan (Trp) is converted in 2 steps to L-kynurenine, and then converted via 2 steps to kynurenic acid. In HepG2, Only LPV targeted this pathway, increasing both compounds. Tryptophanyl-tRNA synthase is up regulated in response to HepG2 cells treated with Pis (Parker 2005) and this may explain the observed increase in Trp |
| Tyrosine metabolism | Pis affected interconversions of Tyrosine to 4-hydroxyphenylpyruvate via tyrosine aminotransferase or aspartate aminotransferase |
| Valine, leucine and isoleucine degradation | LPV increased all 3 BCAA in HepG2 (L-Leucine, L-Isoleucine, L-Valine), which relates to altered metabolism of glucose and lipids. In adipocytes, these BCAA were decreased, most notably by ATV. Leu is ketogenic forming AcCoA for FA ketone bodies and fatty acids. Val is glucogenic; and Ile is glucogenic and ketogenic. |
| Fructose and mannose metabolism | Fructose predominates over glucose in adipose and most frucose is metabolized to beta-D-Fructose 6-phosphate (F6P) accounting for its increase with all Pis. As glucose was decreased in adipose with Pis. As glucose was decreased in adipose with Pis, there is thus less competitive inhibition from glucose for phosphorylation via hexokinase and this also explains the increase in F6P. In HepG2, ther were no changes to F1P or F6P. Glyceraldehyde is generated from Fructose 1P, principally in the liver; its levels were decreased with all Pis in adipocytes |
| Glycolysis/ Gluconeo- genesis | All Pis decreased adipocyte (S)-Lactate (lactate), which is consistent with there being less alpha-D-glucose (Fructose and mannose metabolism) for conversion to lactate. Adipose tissue is known to be a source of lactate |
| | Pis inhibit G3PDH (leading to decreased sn-Glycerol 3-phosphate-G3P from DHAP in HepG2 and adipocytes). The decrease in G3P may cause a compensatory conversion of phosphoenolpyruvate (PEP) and 3-phospho-D-glycerate-3PG (both are decreased) to DHAP to support glyceroneogenesis. LPV decreased G3P most severely in adipocytes. Alternatively, PEP could be altered via A-type pyruvate kinase-PK in adipose, which is under some covalent modification control (e.g., by F16BP), and converts PEP to pyruvate |
| | alpha-D-glucose is decreased in adipocytes, similarly with ATV and LPV. This likely relates to decreased glucose uptake via insulin-regulated GLUT4, partly consistent with literature (Noor et al. 2006). DRV did not significantly affect glucose levels in adipocytes. Changes in adipocyte glucose could affect fat-derived chemocytokines which affect fat mass and distribution. Changes in glucose with DRV and LPV could relate to increased gluconeogenesis, via PI-mediated increases in PEPCK (via ATF4). |

*Fig. 12H*

| SUMMARY (Pathway-centric) | |
|---|---|
| Fatty acid metabolism | In adipocytes, observed increase in saturates tetradecanoic acid (myristate), n-hexadecanoic acid (palmitate), and octadecanoic (steric acid); and MUFAs (9Z)-Hexadecenoic acid (16:1n7) and (9Z)-Octadecenoic acid (18:1n9). These FA are common acyl constituents of TAG. The increase in FFA could be due to: enhanced uptake of FA from media; less secretion of FA into media (the opposite of what is expected with PI); decreased -oxidation; or impaired ability to acylate the FA onto glycerol. The large decrease in G3P (itself resulting from decreased G3PDH from DHAP) suggests an inability to provide adequate glycerol for glyceroneogenesis and TAG information. |
| Glycerolipid metabolism | O-Acetylcarnitine (ALC) was increased by Pis in HepG2 and adipocytes. ALC is a marker for keytone body production, which can result in the fasted metabolic state when OAA is |
| | Glycerate may decrease in HepG2 and adipocytes due to metabolic adaptions to G3PDH inhibition |
| | sn-Glycerol 3-phosphate (G3P) is decreased in both HepG2 and adipocytes, consistent with PI-reduction in G3PDH. The reduction is most severe with LPV in adipocytes, suggesting glycerol could become limiting for TAG production. As G3P is a marker for adipocyte differentiation, Pis may inhibit maturation od adipocytes in vivo, contributing to lipodystrophy (Vernoche et al. JBC 280: 2238, 2005) |
| | The decrease in MAGs such as monopalmitin and 1-stearoyl-rac-glycerol in HepG2 with DRV and LPV could result from numerous pathway modulations that acylate glycerol backbones to form TAGs. For example, Pis are known to induce DAGAT, which converts DAGs to TAGs |
| Glutathione metabolism/ Oxidative Stress/ Pentose phosphate pathway/ Purine metabolism | There was evidence that glutathione metabolism and oxidative stress were induced by Pis. GSH (Glutathione) is reduced with ATV and DRV, and increased with LPV in HepG2 and decreased slightly with ATV and DRV in adipocytes. A decrease in GSH and a decrease in the GSH/GSSG ratio is a marker of oxidative stress. GST is up regulated in response to ER-stress, resulting in conjugation of GSH to substrates such as oxidized lipids and the Pis and this may contribute to reductions in GSH. |
| | Oxidized glutathione (GSSG) was increased with LPV in HepG2, which is a marker of oxidative stress |
| | Gamma-L-Glutamyl-L-cysteine is increased with LPV in hepatocytes. It is formed from GSH via action of g-glutamyl transpeptidase, forming g-glutamyl AA. |
| | 5-oxoproline is formed from g-glutamyl AA via action of g-glutamyl cyclotransferase and is a marker for GSH kinetics. |
| | 6-phosphogluconate and D-Ribulose 5-phosphate were decreased in HepG2 with DRV, so less NADPH is generated for conversion od GSSG to GSH. This is consistent with decreased GSH and may be ER-stress related. In adipocytes, all drugs decreased 6-phosphogluconate. |
| | Deoxyguanosine (2-deoxyguanosine) is formed from GMP-guanosine-guanine- or from dGTP-dGDP-dGMP- reactions. 2-deoxyguanosine is converted to the DNA damage marker 8-hydroxy-deoxyguanosine (8-OHdG), consistent with PI-induced cytotoxicity. Deoxyguanosine was increased in adiocytes |

*Fig. 12I*

METHODS OF IDENTIFYING BIOCHEMICAL PATHWAYS

RELATED APPLICATIONS

This application claims priority to U.S. Provisional Application No. 60/845,045, filed on Sep. 15, 2006, the entire contents of which are hereby incorporated herein by reference.

BACKGROUND

Living organisms are autonomous chemical systems which include diverse sets of small molecules. Small molecules found in living systems include, for example, sugars, fatty acids, amino acids, nucleotides, and intermediates of metabolic and signaling pathways. Sugars are a primary source of chemical energy for cells. The cells break the sugars down through a series of oxidative reactions to small sugar derivatives and, ultimately, $CO_2$ and $H_2O$. Fatty acids are used for both energy storage and as major components of cellular membranes. Amino acids are the building blocks of proteins. Nucleotides are involved in intracellular signaling, energy transfer, and as the monomers of the information macromolecules, RNA and DNA.

The cellular small molecules are, generally, composed of six elements (C, H, N, O, P, S). If water is excluded, carbon compounds comprise a large majority of the cellular small molecules. The cellular small molecules repeatedly use certain distinctive chemical groups, such as methyl ($CH_3$), carboxyl (COOH) and amino ($NH_2$) groups.

In recent years, scientists have attempted to study cells and living systems through the cataloging of the entire genome of organisms through genomics, and the entire proteinome through proteomics. Metabolomics is the study of the small molecules present in a particular organism or a portion there of. Metabolomics has the potential to complement proteomics and genomics, as well as make an independent contribution to the global understanding of systems biology, from individual cells to entire populations of organisms.

SUMMARY

Pharmaceutical companies spend millions, if not billions, of dollars developing what they hope to be, for example, the next blockbuster drug or a new cure for a previously incurable disease or disorder. The process for developing drugs from initial screening, to optimizing the structure activity profile, to lead optimization and validation, and to clinical trials is expensive and time consuming. Unanticipated affects of pharmaceutical compounds can have serious consequences, such as death for patients and serious public relations issues and loss of revenue for the pharmaceutical companies.

There is an unmet need for a comprehensive method of evaluating compounds for both expected (e.g., on-target) and unexpected (e.g., off-target affects). The current products on the market are limited to screening only particular pathways and lack comprehensive screening capabilities which detect a plethora of expected and unexpected affects of the candidate compounds. Therefore, there is a great demand for a better way to detect potential negative or detrimental affects well before the drugs enter the marketplace. The methods of this invention meet this need using a unique combination of metabolomics and computer technology.

Effective and reliable selection of lead candidates early in drug discovery is currently dependent upon established in vitro models predictive of human on-target and off-target effects. Application of metabolomics to, for example, lysates of drug exposed cultured cells as well as samples from subjects treated with the drugs provides a novel and comprehensive analysis of changes in their biochemical profile. This approach offers a global, unbiased and non-targeted assessment of compound activities across a wide array of biological pathways. Reporting statistically altered metabolites and the biological pathways they affect (regulated up or down) provides a clear view of the drug effects. Interpretation of these results reveal the biological impact of these changes and, through comparison, those compounds demonstrating the most appropriate and targeted activities can be selected for continued development.

The invention pertains, at least in part, to methods of using metabolomics to expedite drug discovery and development. The invention, at least in part, provides a means to select and advance the most selective lead compounds from a series of chemical candidates based on metabolomic profiles. The metabolomic profiles contain data regarding both expected or intended (e.g., on-target) and unexpected or unintended (e.g., off-target) affects of the compound. The metabolomic profile of a compound not only helps a pharmaceutical company to select the best lead compound for their purposes, but the profile may also facilitate positioning and/or repositioning by identifying affects which may identify new indications for compound. The methods of the invention can also help companies determine what constitutes an effective amount (or dose) of a drug and appropriate therapeutic windows for its use.

In one embodiment, the invention pertains, at least in part, to a method for identifying biochemical pathways affected by an agent. The method includes obtaining a small molecule profile of an assay treated with the agent, and comparing the small molecule profile to a standard small molecule profile; identifying components of the small molecule profile affected by the agent; and identifying biochemical pathways associated with said components, thus identifying biochemical pathways affected by the agent.

In another embodiment, the invention also pertains to a method for identifying biochemical pathways affected by an agent. The method includes administering an agent to a subject; obtaining a post-administration sample from the subject; detecting a small molecule profile of the post-administration sample; identifying components of said post-administration small molecule profile affected by the agent; and identifying biochemical pathways associated with the components.

In another embodiment, the invention also pertains to a method for positioning an agent. The methods include obtaining a small molecule profile of a sample from an assay treated with the agent; comparing the small molecule profile to a standard small molecule profile; identifying components of the small molecule profile affected by the agent; identifying biochemical pathways associated with said components; using the identified biochemical pathways to identify a therapeutic use for the compound, thus positioning the agent.

In one embodiment, the invention also pertains, at least in part, to methods for determining an advantageous alternate form of an agent. The method includes obtaining a first small molecule profile of a sample from a subject treated with a first alternate of the agent; obtaining a second small molecule profile of a sample from a second subject treated with a second alternate form of the agent; comparing the first small molecule profile to the second small molecule profile; identifying components of the small molecule profiles affected by the alternate form of the agent; identifying biochemical pathways associated with the components; and using the identified biochemical pathways to identify an advantageous alternate form, thus determining an advantageous alternate form of the agent.

In another embodiment, the invention also pertains to a system for the development of lead compounds. The system includes a collection of data that describes multiple biochemical pathways. Each biochemical pathway description identifies multiple compounds associated with the biochemical pathway. The system also includes a data acquisition apparatus that processes an assay following the addition of an agent to the assay in order to determine the effect of the agent on the assay. The processing of the assay generates result data indicating a condition of at least one compound in the assay relative to a control. The system additionally includes an analysis facility that executes on a computing device. The analysis facility is used with the collection of data describing the biochemical pathways to identify at least one biochemical pathway affected by the indicated condition of the at least one compound. In one aspect, the analysis facility provides a score that allows ranking of agents/compounds. In certain embodiments, no biochemical pathways may be affected by the addition of the agent. For example, when the target is not present in the assay (e.g., a cell line), it is possible that an agent may not affect any of the biochemical pathways in the assay and no biochemical pathways will be identified.

In one embodiment, the invention also pertains to a method of identifying lead compounds. The method includes providing, in a computing device, a collection of data describing multiple biochemical pathways. Each biochemical pathway description identifies multiple compounds associated with the biochemical pathway. The method also adds an agent to an assay and processes the assay to acquire result data that indicates the effect of the addition of the agent on the assay. The result data indicates a condition of at least one compound in the assay relative to a control. The method also identifies, using the collection of data describing the biochemical pathways, at least one biochemical pathway affected by the indicated condition of the at least one compound. In one aspect, a score is provided that allows ranking of agents/compounds.

In another embodiment, a method of identifying lead compounds includes the step of providing, in a computing device, a collection of data describing multiple biochemical pathways. Each biochemical pathway description identifies multiple compounds associated with the biochemical pathway. The method also adds an agent to an assay and processes the assay to acquire result data indicating the effect of the addition of the agent on the assay. The result data indicates a condition of at least one compound in the assay relative to a control. The method also identifies programmatically without user assistance, using the collection of data describing the biochemical pathways, at least one biochemical pathway affected by the indicated condition of the at least one compound. In one aspect, a score is provided that allows ranking of agents/compounds.

BRIEF DESCRIPTION OF THE DRAWINGS

The invention is pointed out with particularity in the appended claims. The advantages of the invention described above, as well as further advantages of the invention, may be better understood by reference to the following description taken in conjunction with the accompanying drawings, in which:

FIG. 4 is an exemplary concise report that may be produced by an embodiment of the present invention to display metabolite data for biochemical pathways identified as affected by the addition of an agent to an assay;

FIG. 11 shows four Z-plots which show the effect of three test compounds on hepatocytes and adipocytes; and FIGS. 12A-12I contain other exemplary concise reports which may be produced by the methods of the invention to display metabolite data for biochemical pathways identified as affected by the addition of an agent to an assay.

DETAILED DESCRIPTION

Figure 1:
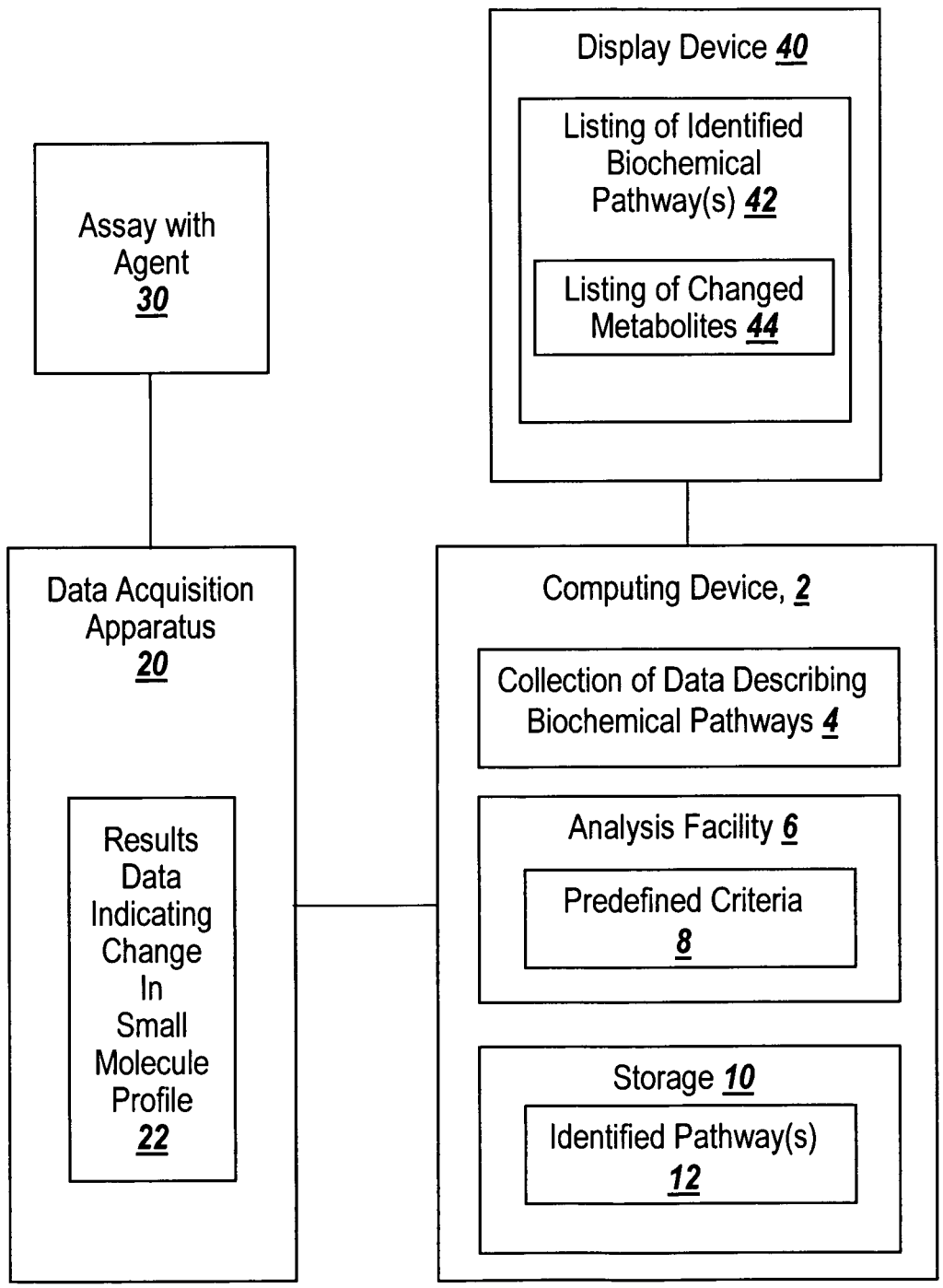
FIG. 1 depicts an environment suitable for practicing an embodiment of the present invention.

The invention provides, at least in part, detailed information about an agent's effects on biochemical processes using advanced metabolomic analyses. Comparative evaluations between agents provide insight into each agent's quantitative and qualitative specificity. Results from concurrent analysis of agents with known side effects and/or marketed drugs can provide insight into predicting the safety and clinical performance of the agents.

The invention also provides a non-targeted analysis which offers a unique opportunity to corroborate each agent's putative target activity. Based on these data, a clear selection of the most selective lead compounds for advancement into further stages of development can be accomplished.

In one embodiment, the invention pertains, at least in part, to a method for identifying biochemical pathways affected by an agent. The method includes obtaining a small molecule profile of a sample from an assay treated with the agent, and comparing the small molecule profile to a standard small molecule profile; identifying components of the small molecule profile affected by the agent; and identifying biochemical pathways associated with said components, thus identifying biochemical pathways affected by the agent.

The term "agent" includes small molecules, candidate drug compounds (e.g., therapeutic agents, potential anti-infective, antibiotic, antimicrobial, anti-inflammatory, cytostatic, cytotoxic, antiviral, anesthetic agents, prophylactic compounds, etc.), and macromolecules (e.g., antibodies, proteins, peptidomimetic, small peptides, nucleic acids, polysaccharides, etc.). The term "agent" includes any compound or, in certain embodiments, combinations of compounds which may be administered to an assay of the invention to yield a small molecule profile. Preferably, the agent is administered to the assay of the invention in an amount such that it is possible to identify biochemical pathways affected by the agent. The term "agent" may also include toxins and other substances which may cause an adverse effect. The term also includes prodrugs and salt forms. In addition, it may be advantageous to administer the agent in combination with a pharmaceutically acceptable carrier, especially when administered to a living subject.

The term "agent" also includes candidate therapeutic compounds and lead therapeutic compounds. Candidate therapeutic compounds (or "candidate compounds" include, for example, compounds which are being tested using the methods of the invention. The methods of the invention may be used to identify, for example, both expected (e.g., intended, on-target) and unexpected (e.g., unexpected, e.g., off-target) effects of the candidate compounds. Expected effects include effects which are related to or otherwise associated with the therapeutic indication for which the compound was intended. For example, expected effects of a candidate anti-cancer therapeutic may include, for example, that compound's cytotoxicity towards tumor cells. Unexpected effects may include, for example, systems and pathways which the particular candidate compound was not designed to treat and may be negative (e.g., detrimental) or positive (e.g., therapeutic). For example, negative unexpected effects of a candidate anti-cancer compound may be, for example, liver damage. In certain embodiments, positive unexpected effects of candidate compounds may indicate other uses for a particular compound. For example, a particular compound which was designed for treating heart disease may have effects that improve bone density. This candidate compound may then be repositioned to treat osteoporosis in addition to, or, alternatively, to replace heart disease.

The term "lead compounds" include compounds, e.g., therapeutic compounds, selected for their potential to treat, cure, prevent, or otherwise contribute beneficially to a particular disease, disorder, or otherwise aid a particular subject. The lead compounds maybe selected from the candidate compounds for many reasons, including, but not limited to, efficacy (in vivo and/or in vitro), few or less serious negative unexpected (e.g., detrimental off-target) effects, etc.

The term "assay" includes both in vitro and in vivo assays. Examples of in vitro assays include cellular assays using cell lines known in the art. The cell lines may be cell lines which have been genetically altered or otherwise selected to mirror particular disease states or express particular traits. Examples of cell lines that can be used in the methods of the invention include those known in the art. For cell based assays, the agent may be administered to the cells in an amount ranging from about 0.01 fold to about 100 fold, about 0.1 fold to about 50 fold, about 1 fold to about 40 fold, or about 5 fold to about 20 fold, or about 10 fold the $IC_{50}$ or $EC_{50}$ of the agent. The agent may be administered to the cells once, twice, three times, four times, five times or more.

Examples of cells which can be used include human hepatocytes (e.g., primary or preserved), human preadipocytes (e.g., primary or otherwise), HepG2 cells, human skeletal myocytes, etc. Furthermore, the cells or progenitor cells may also be removed from particular subjects. Other examples of cell lines which may be used in the methods of the invention include, but are not limited to, monkey kidney CV1 line transformed by SV40 (COS-7, ATCC CRL 1651); human embryonic kidney line (293 or 293 cells subcloned for growth in suspension culture, Graham et al., J. Gen Virol., 36:59 [1977]); baby hamster kidney cells (BHK, ATCC CCL 10); Chinese hamster ovary cells/-DHFR (CHO, Urlaub and Chasin, Proc. Natl. Acad. Sci. USA, 77:4216 [1980]); mouse sertoli cells (TM4, Mather, Biol. Reprod., 23:243-251 [1980]); monkey kidney cells (CV1 ATCC CCL 70); African green monkey kidney cells (VERO-76, ATCC CRL-1587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 [1982]); MRC 5 cells; FS4 cells; human hepatoma line (Hep G2); and plant cell cultures (e.g., cell lines derived from monocot (e.g., maize, rice, etc.) or dicot (e.g., tobacco, sunflower, etc.) plant species).

In another embodiment, the term "assay" includes administering the compound or combination of compounds to a subject such as a plant, animal, yeast, or bacteria. The term "subject" includes both non-genetically modified and genetically modified organisms. In one embodiment, the subject is a rodent (e.g., mouse, rat, guinea pig, etc.). In another embodiment, the "subject" is a rabbit, goat, cow, pig, sheep, monkey, gorilla, horse, cat, dog, or, preferably, a human.

In certain embodiments, the assay includes administering the agent to a human during clinical trials of the agent. The samples may be obtained from the subject during, for example, an appropriate phase of clinical trials. For example, the samples may be obtained from the subject during Phase 1 studies (e.g., studies relating to the safety of the agent), Phase 2 studies (e.g., studies related to the safety and efficacy of the agent), Phase 3 studies (e.g., studies related to the efficacy and safety of the agent), or in Phase 4 studies (e.g., in life surveillance).

The human subject may be healthy, suffering from an unrelated disease or disorder unrelated to the potential therapeutic benefit of the agent, or suffering from a disease or disorder that is within the intended therapeutic scope of the agent. The human may be male or female, pregnant or non-pregnant, a newborn (under 3 months in age), an infant (under 1 year in age), a young child (from about 1 to about 10), an adolescent (about age 10 to about age 19), a young adult (about age 20 to about age 40), middle aged (about age 40 to about age 60), an older adult (about above age 60), or elderly (above about age 80).

The term "biochemical pathway" includes those pathways described in Roche Applied Sciences' "Metabolic Pathway Chart" or other pathways known to be involved in metabolism of organisms. Examples of biochemical pathways include, but are not limited to, carbohydrate metabolism (including, but not limited to, glycolysis, biosynthesis, gluconeogenesis, Kreb's Cycle, Citric Acid Cycle, TCA Cycle, pentose phosphate pathway, glycogen biosynthesis, galactose pathway, Calvin Cycle, aminosugars metabolism, butanoate metabolism, pyruvate metabolism, fructose metabolism, mannose metabolism, inositol phosphate metabolism, propanoate metabolism, starch and sucrose metabolism, etc.), energy metabolism (e.g., oxidative phosphorylation, reductive carboxylate cycle, etc.), lipid metabolism (including, but not limited to, triacylglycerol metabolism, activation of fatty acids, β-oxidation of polyunsaturated fatty acids, β-oxidation of other fatty acids, α-oxidation pathway, de novo biosynthesis of fatty acids, cholesterol biosynthesis, bile acid biosynthesis, fatty acid metabolism, glycerolipid metabolism, glycerophospholipid metabolism, sphingolipid metabolism, etc.) amino acid metabolism (including, but not limited to, glutamate reactions, Kreb-Henseleit urea cycle, shikimate pathway, phenylalanine and tyrosine biosynthesis, tryptophan biosynthesis, metabolism and/or degradation of particular amino acids (e.g., alanine, aspartate, arginine, proline, glutamate, glycine, serine, threonine, histadine, cysteine, methionine, phenylalanine, tryptophan, tyrosine, valine, leucine, or isoleucine metabolism and/or degradation, etc.), biosynthesis of amino acids (e.g., lysine and tryptophan biosynthesis, etc.), folate biosynthesis, one carbon pool by folate, pantothenate and CoA biosynthesis, riboflavin metabolism, thiamine metabolism, vitamin B6 metabolism, β-alanine methabolism, D-glutamine and D-glutamate metabolism, glutathionine metabolism, cyanoamino acid metabolism, N-glycan biosynthesis, benzoate degradation, alkaloid biosynthesis, selenoamino acid metabolism, purine metabolism, pyrimidine metabolism, phosphatidylinositol signaling system, neuroactive ligand-receptor interaction, energy metabolism (including, but not limited to, oxidative phosphorylation, ATP synthesis, photosynthesis, methane metabolism, etc.), phosphogluconate pathway, oxidation-reduction, electron transport, oxidative phosphorylation, respiratory metabolism (respiration), HMG-CoA reductase pathway, porphyrin synthesis pathway (heme synthesis), nitrogen metabolism (urea cycle), nucleotide biosynthesis, DNA replication, transcription, and translation. It also includes portions of these pathways and individual chemical reactions.

The term "sample" includes preparations from which it is possible to obtain a small molecule profile representative of the assay. The term "sample" includes, for example, cellular extracts from in vitro assays. For in vivo assays, the sample may include or be derived from a subject's blood, serum, intracellular fluid, cerebrospinal fluid, saliva, urine, tissue (e.g., muscle tissue, fatty tissue, etc.), skin, hair, aminionic fluid, etc. The sample may be comprised of any material from the assay from which a small molecule profile can be determined. For in vivo assays, the sample may be from one particular organism or numerous organisms, e.g., numerous healthy organisms or numerous organisms having a particular disorder.

The term "small molecules" includes organic and inorganic molecules which are present in the sample. The term does not include large macromolecules, such as large proteins (e.g., proteins with molecular weights over 1,000, 2,000, 3,000, 4,000, 5,000, 6,000, 7,000, 8,000, 9,000, or 10,000), large nucleic acids (e.g., nucleic acids with molecular weights of over 1,000, 2,000, 3,000, 4,000, 5,000, 6,000, 7,000, 8,000, 9,000, or 10,000), or large polysaccharides (e.g., polysaccharides with a molecular weights of over 1,000, 2,000, 3,000, 4,000, 5,000, 6,000, 7,000, 8,000, 9,000, or 10,000). The term "small molecules" includes signaling molecules and intermediates in the chemical reactions that transform energy derived from food into usable forms. Examples of small molecules include sugars, fatty acids, amino acids, amino acid derivatives, nucleotides, derivatives of nucleotides, steroids, vitamins, cofactors, intermediates formed during biochemical processes, and other small molecules found within the sample. The term also includes non-native substances such as metabolites of the agent administered to the subject or the agent itself.

Other examples of small molecules which may be found in plasma of a subject include, but are not limited to, 5-oxoproline; 5'-methylthioadenosine; N1-methylnicotinamide; 1-methylhistidine; 1,25-dihydroxycholecalciferol; 1,25-dihydroxyvitamin D; 11-deoxycortisol; 4-guanidinobutanoate; 17-hydroxyprogesterone; 2-oxoglutarate; 2,5,7,8-tetramethyl-2-(β-carboxyethyl)-6-hydroxychroman (α-CEHC); 2,7,8-trimethyl-2-(β-carboxyethyl)-6-hydroxychroman (γ-CEHC) 2'-deoxyuridine; 24,25-dihydroxycholecalciferol; 24,25-dihydroxyvitamin D; 24S-hydroxycholesterol; 25-hydroxycholecalciferol; 25-hydroxyvitamin D2; 25-hydroxyvitamin D3; 25,26-dihydroxyvitamin D; 3-hydroxybutyrate; 3-M-tyramine; 3-M-tyramine (sulfate conjugated); 3-M-tyrosine; 3-M-tyrosine (sulfate conjugated); 3-methylhistidine; 3'-monoiodothyronine (3'Ti); 3α-hydroxy-5α-pregnan-20-one (3α,5α-tetrahydro-P) (allopregnanolone); 3β-hydroxy-5α-pregnan-20-one (alloepipregnanolone); 3β-hydroxy-5β-pregnan-20-one (epipregnanolone); 5-hydroxyindoleacetic acid (5HIAA), 5α-pregnane-3,20-dione (5α-dihydro-P); 5β-pregnane-3,20-dione; acetate; 4-acetaminophen sulfate; acetoacetate; O-acetylcamitine; N-acetyl-D-glucosamine 6-phosphate; N-acetylneuraminate; N-acetyl-L-aspartate; 1-acylglycerol; adenine; adenosine, adenosine phosphates (e.g., AMP, ADP, ATP, etc.); S-adenosyl-L-methionine; adrenaline; alanine; aldosterone; α-aminobutyric acid; 2-aminoacridone; L-aspartate; α-glucose; α-ketoglutarate (2-ketoglutarate); L-aminoadipate; ammonia, androstenedione; arabitol; arginine; L-arginine; N-(L-arginino) succinate; asparagine; aspartate; L-aspartate; L-aspartyl-L-phenylalanine; asymmetric dimethylarginine (ADMA); β-galactose; β-glucose; bestatin; bilirubin; cadaverine; camitine; carotene; choline; citrate; citrulline; L-citrulline; cortisol; creatine; creatinine; cyanide; cysteine; cystine; cytidine 5'monophosphate; cytidine; D-arabinitol; dehydroepiandrosterone (DHEA); dehydroepiandrosterone sulfate (DHEA-S); deoxyguanosine; deoxyuridine; diaminopimelate; diethanolamine; dihydrouracil; dihydroxyphenylacetic acid; dihydroxyphenylglycol; dihydroxyphenylglycol (sulfate conjugated); 2,2-dimethylsuccinate; dimethylamine; dopamine; dopamine (sulfate conjugated); epinephrine; epinephrine (sulfate conjugated); estradiol; estrone; ethanolamine phosphate; ethylmalonic acid; folic acid; folate; formate; free fatty acids; fructosamine; D-fructose-1-phosphate; D-fructose-6-phosphate; β-D-fructose-6-phosphate; fucose; fumarate; galactitol; GDP-mannose; glucose; α-D-glucose; D-glucono-1,5-lactone; glutamate; L-glutamate; glutamine; L-glutamine; γ-L-glutamyl-L-cysteine; γ-L-glutamyl-L-glutamine; glutathionine; oxidized glutathionine; glycerol; glycyl sarcosine; glycerol D-phosphate; glycero-3-phosphocholine; glycerate; D-glycerate; glyceraldehyde; D-glyceraldehyde; glycerate; D-glycerate; glycine; guanosine; guanosine-5-diphospho-D-mannose; hexadecanoic acid; (9Z)-hexadecanoic acid; HDL (high density lipoprotein) cholesterol; DL-hexanoyl carnitine; histamine; histidine; L-histidine; L-histidinol; histidyl-proline diketopiperazine [cyclo(His-Pro)]; homocysteine; homocysteine-thiolactone; homoserine; homovanillic acid (HVA); hydroxyproline; (p-hydroxyphenyl) lacatate; DL-α-hydroxystearate; hydroxanthine; trans-b-hydromuconate; hypoxanthine; 3-(4-hydroxyphenyl) pyruvate; 3-hydroxybenzoate; L-β-imidazolelactate; inosine; inositol 1-phosphate; isobutyrate; isoleucine; L-isoleucine; 2-isopropylmalate; L-3,4-dihydroxyphenylalanine (DOPA); 2-isopropylmalate; L-3,4-dihydroxyphenylalanine (sulfate conjugated)(DOPA-S); 3-(4-hydroxyphenyl) pyruvate; p-hydroxybenzaldehyde; 1H-imidazole-4-ethanamine; kynurenine; L-kynurenine; kynurenic acid; lactate; LDL (low density lipoprotein) cholesterol; lactose; leucine; L-leucine; lysine; maltose; mannose; D-mannose; D-mannose 6-phosphate; mannitol; mesaconate; metanephrine; metanephrine (sulfate conjugated); methionine; methoxyhydroxy-phenylglycol; methoxyhydroxy-phenylglycol (sulfate conjugated); methylamine; 2-methylhippuric acid; methylmalonic acid; 3-methyl-2-oxobutanoic acid; myo-inositol; nitrate; nitrite; non-esterified fatty acids (NEFA); norepinephrine (noradrenaline); norepinephrine (sulfate conjugated); norleucine; normetanephrine; normetanephrine (sulfate conjugated); mesaconate; meso-erythritol; Nτ-methylhistamine (1-methylhistamine); (S)-malate; malonate; D-mannose; D-mannose-6-phosphate; ornithine; 2-oxoglutarate; palmitate; pantothenate; phenylalanine; L-phenylalanine; phosphoenolpyruvate; O-phospho-L-serine; octadecanoic acid; (9Z)-octadecanoic acid; oxalate; 5-oxoproline; orthophosphate; phenylacetylglutamine; picolinamide; 3-phospho-D-glycerate; 6-phospho-D-gluconate; pregnenolone; progesterone; proline; L-proline; putrescine; pyroglutamic acid; pyruvate; pyridoxine; pyridoxamine; ribitol; D-ribulose-5-phosphate; riboflavin; serine; L-serine; serotonin (5-HT); sorbitol; D-sorbitol; sphingosine; succinate; succinic acid; 5-sulfosalicylate; symmetric dimethylarginine (SDMA); taurine; testosterone; tetradecanoic acid; thiamin; thiamin monophosphate; threonine; L-threonine; thymidine; thyroxine (T4); total cholesterol; triglycerides; triiodothyronine (T3); trimethyl amine oxide (TMAO); trimethylamine; tryptophan; L-tryptophan; tyrosine; L-tyrosine; uracil; urea; uric acid; uridine; uridine-diphosphate-N-acetylmuraminate; valine; L-valine; vanillylmandelic acid; vitamin A; vitamin B12; vitamin B6; vitamin C; vitamin D2; vitamin D3; vitamin E; xanthine; xanthosine; xyulose; and xylitol. Other compounds can also be found using the methods of the invention. Other metabolites are known in the art and can be found in the Human Metabolome Database.

Other examples of small molecules which may be found in the urine of a subject include, but are not limited to, 1-methyladenosine; 1-methylhistamine; 1-methylhistidine; 1-methylimidazoleacetic acid; 2-deoxytetronate; 2-hydroxyadipate; 2-hydroxyglutarate; 2-hydroxyisobutyrate; 2-methylcitrate; 2-methylglutarate; 2-methyl-3-(3'-3'-carboxymethylpropyl)-1,4-naphthoquinone (5C-aglycone); 2-methyl-3-(5'-carboxy-3'-methyl-2'-pentenyl)-1,4-naphthoquinone (7C-aglycone); 2-oxoadipate; 2-oxoglutarate; 2,4-dichlorophenol; 2,5-furandicarboxylate; 3-deoxytetronate; 3-hydroxyadipate; 3-D-hydroxybutyrate; 3-hydroxyisobutyrate; 3-hydroxypropionate; 3-hydroxyisovalerate; 3-hydroxysebacate; 3-hydroxysuberate; 3-hydroxy-2-methylbutyrate; 3-hydroxy-3-methylglutarate; 3-methoxybenzene-propionate; 3-methylglutarate; 3-methylhistidine; 3-methyluridine; 3,4-dihydroxycinnamate; 3,4-dihydroxyphenylacetic acid; 4-deoxytetronate (threo); 4-heptanone; 4-hydroxybenzoate; 4-hydroxycyclohexyl-carboxylate; 4-hydroxymandelate; 4-hydroxy-3-methylbenzoate; 4,6-diamino-5-formamidopyrimidine; 5-deoxyadenosine; 5-hydroxycaproate; 5-hydroxydopamine; 5-hydroxyindoleacetic acid (5-HIAA); 5-hydroxymethylfuranoate; 5-methylcytidine; 5-oxoproline; 6-hydroxydopamine; 6-keto-prostaglandin-F1 α; 4-deoxytetronate (erythro); 8-hydroxy-2'-deoxyguanosine; 17-hydroxycorticosteroids; 17-ketogenic steroids; acetoacetate; acetone; acetylcamitine; acylcarnitine; adenosine; adipate; alanine; α-aminoadipate; α-amino-N-butyrate; α-ketoglutarate; ammonia; anserine; arginine; arsenic; asparagine; aspartate; azelate; benzenedicarboxylate; β-alanine; β-aminoisobutyrate; β-aminoisobutyric acid; betaine; β-hydroxyisovaleric acid; beta-methylcrotonylglycine; β-ureidoisobutyric acid; β-ureidopropionic acid; biopyrrins; biotin; biotin-d1-sulfoxide; bisnorbiotin; bisnorbiotin methyl ketone; biotin sulfone; camitine; camosine; cis-aconitate; citramalate; citrate; citrulline; cortisol; creatine; creatinine; cystathionine; cystathionine ketimine; cysteine; cystine; cytidine; dihydrothymine; dihydrouracil; dihydroxyacetone; dimethylamine; dopamine; ethanolamine; epinephrine; erythronate; ethylhydracrylate; ethylmalonate; formate; free cortisol; fumarate; furoate; γ-aminobutyrate; glucose; glutamate; glutamine; glutarate; glycerate; glycine; glycine betaine; glycolate; glycolithocholic acid sulfate; guanosine; hexadecanoate; hippurate; histidine; homocystine; homovanillate; homovanillic acid; hydroxyproline; imidazoleacetic acid; indoleacetate; indoxyl sulfate; isocitrate; isoleucine; lactate; lanthionine ketimine; leucine; lysine; m-cresol; m-hydroxyphenylhydracrylate; m-tyramine; malate; metanephrine; methionine; methionine sulfoxide; methylmalonic acid; methylsuccinate; mevalonic acid; N-acetylaspartate; N π-methylimidazoleacetic acid; N τ-methylimidazoleacetic acid; N1-methylnicotinamide; N,N-dimethylglycine; N2,N2-dimethylguanosine; norepinephrine; normetanephrine; o-cresol; ornithine; oxalate; p-cresol; p-hydroxyphenylacetate; p-hydroxyphenyllactate; p-hydroxyphenylpyruvate; p-octopamine; p-synephrine; p-tyramine; phenol; phenylalanine; phosphoethanolamine; phosphoserine; pimelate; porphobilinogen; proline; proline betaine; prostaglandin (PG) E2; prostaglandin (PG) F2 α; serotonin; suberate; serine; sarcosine; quinolinate; pyruvate; pyroglutamate; pseudouridine; succinate; succinic acid; taurine; tiglylglycine; threonate; threonine; thromboxane B2; thymine; 17-ketosteroids; metanephrines; trimethylamine; trimethylamine oxide; tryptophan; tyrosine; uracil; urea; uric acid; uridine; valine; vanillic acid; vanillactic acid; vanillylmandelate; and vanillylmandelic acid (VMA).

The language "small molecule profile" includes an inventory of small molecules (in tangible form or computer readable form) within a sample from an assay or any derivative fraction thereof, that is necessary and/or sufficient to provide information to a user for its intended use within the methods described herein. The inventory would include the quantity and/or type of small molecules present. The ordinarily skilled artisan would know that the information which is necessary and/or sufficient will vary depending on the intended use of the "small molecule profile." For example, the "small molecule profile," can be determined using a single technique for an intended use but may require the use of several different techniques for another intended use depending on such factors as the disease state involved, the types of small molecules present in a particular sample, etc. In a further embodiment, the small molecule profile comprises information regarding at least 10, at least 25, at least 50, at least 100, at least 200, at least 300, at least 500, at least 1000, or at least 2000 small molecules.

The small molecule profiles can be obtained using HPLC (Kristal, et al. *Anal. Biochem.* 263:18-25 (1998)), thin layer chromatography (TLC), or electrochemical separation techniques (see, WO 99/27361, WO 92/13273, U.S. Pat. No. 5,290,420, U.S. Pat. No. 5,284,567, U.S. Pat. No. 5,104,639, U.S. Pat. No. 4,863,873, and U.S. RE32,920). Other techniques for determining the presence of small molecules or determining the identity of small molecules of the cell are also included, such as refractive index spectroscopy (RI), Ultra-Violet spectroscopy (UV), fluorescent analysis, radiochemical analysis, Near-InfraRed spectroscopy (Near-IR), Nuclear Magnetic Resonance spectroscopy (NMR), Light Scattering analysis (LS), gas-chromatography-mass spectroscopy (GC-MS), liquid chromatography, gas chromatography, mass spectrometry, and liquid-chromatography-mass spectroscopy (LC-MS) and other methods known in the art, alone or in combination.

These techniques can be used to detect both electrochemically active molecules as well as electrochemically neutral molecules. The methods of the invention allow for the detection of compounds present in samples at concentrations as low as about 1 nM. In one embodiment, the techniques of the invention allow for the detection of at least 10, at least 25, at least 50, at least 100, at least 200, at least 300, at least 500, at least 1000, or at least 2000 small molecules species in a sample. The techniques used in the analysis of the compounds in the sample may be used to detect both electrochemically active molecules as well as electrochemically neutral molecules. In a further embodiment, the invention pertains to techniques which detect about 5% or more, about 10% or more, about 15% or more, about 20% or more, about 25% or more, about 30% or more, about 35% or more, about 40% or more, about 45% or more about 50% or more, about 60% or more, about 70% or more, about 75% or more, about 77.5% or more, about 80% or more, about 82.5% or more, about 85% or more or more of the small molecules of a sample.

HPLC columns equipped with coulometric array technology can be used to analyze the samples, separate the compounds, and/or create a small molecule profiles of the samples. Such HPLC columns have been used extensively in the past for serum, urine and tissue analysis and are suitable for small molecule analysis (Acworth et al., 300; Beal et al., *J Neurochem.* 55, 1327-1339, 1990; Matson et al., *Life Sci.* 41, 905-908, 1987; Matson et al., *Basic, Clinical and Therapeutic Aspects of Alzheimer's and Parkinson's Diseases*, vol II, pp. 513-516, Plenum, N.Y. 1990; LeWitt et al., *Neurology* 42, 2111-2117, 1992; Milbury et al., *J. Wildlife Manag.*, 1998; Ogawa et al., *Neurology* 42, 1702-1706, 1992; Beal et al., *J. Neurol. Sci* 108, 80-87, 1992, Matson et al., *Clin. Chem.* 30, 1477-1488, 1984; Milbury et al., *Coulometric Electrode Array Detectors for HPLC*, pp. 125-141, VSP International Science Publication; Acworth et al., *Am. Lab* 28, 33-38, 1996). HPLC columns equipped with coulometric arrays have been used for the simultaneous analysis of the majority of low-molecule weight, redox-active compounds in mitochondria. (*Anal. Biochem.* 263, 18-25, 1998). Other techniques which are useful for creating the small molecule profiles include GC-MS and LC-MS.

In order to create a small molecule profile, a sample is analyzed to determine the concentration of, for example, several hundred small molecules. Analytical techniques such as liquid chromatography, gas chromatography, mass spectrometry, GC-MS (gas chromatography-mass spectrometry) and LC-MS (liquid chromatography-mass spectrometry) are used to analyze the small molecules. Generally, multiple aliquots are simultaneously, and in parallel, analyzed, and, after appropriate quality control (QC), the information derived from each analysis is recombined. Every sample may be characterized according to many, e.g., several thousand, characteristics, which ultimately may amount to several hundred chemical species of small molecules. The techniques used are able to identify novel and chemically unnamed compounds as well as known compounds.

Generally, the data are analyzed using T-tests to identify small molecules (either known, named compounds or unnamed compounds) present at differential levels in a definable population or subpopulation (e.g., biological samples exposed to an agent or formulation of an agent compared to control biological samples or compared to biological samples exposed to a second agent or formulation of an agent or concentration of an agent) useful for distinguishing between the definable populations (e.g., samples exposed to an agent versus controls not exposed to the agent). Other molecules (either known, named compounds or unnamed compounds) in the definable population or subpopulation are also identified.

Various peaks identified in the analyses (e.g. GC-MS, LC-MS, MS-MS, etc.), including those identified as statistically significant, may be subjected to a mass spectrometry based chemical identification process.

The known compounds may then be mapped to biochemical pathways and the pathways that are affected are determined. Based upon this analysis the physiological impact of the agent can be determined. A report may then be generated which may show the metabolites, pathways and physiological impact of the agent, thus summarizing the biochemical results.

The term "standard small molecule profile" includes small molecule profiles of control samples from similar subjects not treated with the agent or samples from the subjects prior to administeration of the agent. It also includes averaged profiles generated from the study of similar samples from similar organisms or cell cultures, for example.

The term "standard small molecule profile" includes profiles derived from healthy cells or organisms, advantageously from a similar origin as the sample. In one embodiment, the standard profile is an average of many samples of a certain cell type, a certain cell line, a certain organism species and/or a certain sample type or biological fluid (e.g., serum, blood, urine, saliva, CSF, amnionic fluid, etc.). In a further embodiment, the standard small molecule profile can be an average of the profiles obtained from numerous sources, e.g., the standard profile may be an average of small molecule profiles obtained from 2 or more, 10 or more, 20 or more, 50 or more, 100 or more, 200 or more, 500 or more, 1000 or more subjects.

Furthermore, the language "standard small molecule profile" includes information regarding the small molecules of the profile that is necessary and/or sufficient to provide information to a user for its intended use within the methods described herein. The standard profile would include the quantity and/or type of small molecules present. The ordinarily skilled artisan would know that the information which is necessary and/or sufficient will vary depending on the intended use of the "standard small molecule profile." For example, the "standard small molecule profile," can be determined using a single technique for an intended use but may require the use of several different techniques for another intended use depending on such factors as the types of small molecules present in a particular targeted cellular compartment, the cellular compartment being assayed per se., etc. Examples of techniques that may be used have been described above and include, for example, GC-MS, LC-MS, NMR, HPLC, etc.

The term "identifying" includes both automated and non-automated methods of identifying components of the sample small molecule profile which are abberant as compared to the standard small molecule profile. The term "abberrant" includes compounds which are present in greater or lesser amounts in the sample small molecule profile than the standard profile. The compound may be in a statistically significant different amount than in the standard profile.

The term "components" includes those small molecules of the small molecule profile which are present in abberrant amounts compared to the standard small molecule profile.

After the components are identified, the identified components are analyzed using, for example, a database of biochemical pathways to pinpoint the particular pathways affected by a particular agent. Once the biochemical pathways are identified, biological effects of modulating these pathways are determined, including, for example, both expected and unexpected effects.

In another embodiment, the invention also pertains to a method for identifying biochemical pathways affected by an agent. The method includes administering an agent to a subject; obtaining a post-administration sample from the subject; detecting a small molecule profile of the post-administration sample; identifying components of said post-administration small molecule profile affected by the agent; and identifying biochemical pathways associated with the components.

The term "affected" includes any modulation or other change caused by the agent. The term can include both increasing the activity or decreasing the activity of a biological pathway or portion thereof. It includes both upregulation and down regulation and/or increased or decreased flux through the pathway and/or increased or decreased levels of metabolites in the pathway.

In another embodiment, the invention also pertains to a method for positioning an agent. The methods include obtaining a small molecule profile of a sample from an assay treated with the agent; comparing the small molecule profile to a standard small molecule profile; identifying components of the small molecule profile affected by the agent; identifying biochemical pathways associated with said components; using the identified biochemical pathways to identify a therapeutic use for the compound, thus positioning the agent.

The term "positioning" includes finding an appropriate therapeutic use for a compound. It includes, for example, minimizing negative, unexpected (e.g., adverse, off-target) effects and maximizing therapeutic effects which may be expected or unexpected. The term "positioning" also includes "repositioning." "Repositioning" includes methods for finding new therapeutic uses for compounds which had previously been used for a different therapeutic use.

In a further embodiment, the methods of the invention can be used to determine appropriate therapeutic windows for compounds of the invention. The term "therapeutic windows" includes the period of time during an illness or disease when an agent is most useful. For example, after reviewing the biological pathways affected by an agent it may be determined that an agent may be most useful to treat the symptoms or the disease state at the early, mid or late stages of disease development.

In one embodiment, the invention also pertains, at least in part, to methods for determining an advantageous combination of agents. The method includes obtaining a first small molecule profile of a sample from a subject treated with a first combination of agents; obtaining a second small molecule profile of a sample from a second subject treated with a second combination of the agents; comparing the first small molecule profile to the second small molecule profile; identifying components of the small molecule profiles affected by the combination of the agents; identifying biochemical pathways associated with the components; and using the identified biochemical pathways to identify an advantageous combination, thus determining an advantageous combination of the agents.

Examples of combinations of agents include agents which provide additional therapeutic benefit when administered in combination, such as, compounds which treat a particular disease or symptoms or agents which prevent metabolism of a drug with the drug, etc.

The term "advantageous combinations" includes combinations which, for example, are selected to minimize negative unexpected effects of the agents and/or maximize therapeutic effects of the agents.

In one embodiment, the invention also pertains, at least in part, to methods for determining an advantageous alternate form of an agent. The method includes obtaining a first small molecule profile of a sample from a subject treated with a first alternate of the agent; obtaining a second small molecule profile of a sample from a second subject treated with a second alternate form of the agent; comparing the first small molecule profile to the second small molecule profile; identifying components of the small molecule profiles affected by the alternate form of the agent; identifying biochemical pathways associated with the components; and using the identified biochemical pathways to identify an advantageous alternate form, thus determining an advantageous alternate form of the agent.

The term "alternate form" includes different dosages, prodrugs, formulations (e.g., pharmaceutical formulations), pharmaceutical compositions, routes of administration, salt forms, etc.

The term "advantageous alternate forms" includes alternate forms which, for example, are selected to minimize negative unexpected effects of the agent and/or maximize therapeutic effects of the agent. The advantageous alternate forms may be selected based on the number of components affected by a particular form of an agent (e.g., the agent which affects the least number of negative unexpected components.) The first and second subjects may be the same or different. In a further embodiment, the methods of the invention further comprise obtaining small molecule profiles from additional subjects or the same subject treated with the same or different alternate forms of the agent. In a further embodiment, the number of small molecule profiles, subjects, and alternate forms of the agent are selected such that the results are statistically significant.

In one embodiment, the invention also pertains, at least in part, to methods for determining an advantageous dose of an agent. The method includes obtaining a first small molecule profile of a sample from a subject treated with a first dose of the agent; obtaining a second small molecule profile of a sample from a second subject treated with a second dose of the agent; comparing the first small molecule profile to the second small molecule profile; identifying components of the small molecule profiles affected by the dose of the agent; identifying biochemical pathways associated with the components; and using the identified biochemical pathways to identify an advantageous dose, thus determining an advantageous dose of the agent. The first and second subjects may be the same or different.

In yet another embodiment, the invention also pertains, at least in part, to methods for determining an advantageous salt form of an agent. The method includes obtaining a first small molecule profile of a sample from a subject treated with a first salt form of the agent; obtaining a second small molecule profile of a sample from a second subject treated with a second salt form of the agent; comparing the first small molecule profile to the second small molecule profile; identifying components of the small molecule profiles affected by the salt form of the agent; identifying biochemical pathways associated with the components; and using the identified biochemical pathways to identify an advantageous salt form, thus determining an advantageous salt form of the agent. The first and second subjects may be the same or different.

Examples of salt forms of agents which can be used in the methods of the invention include, but are not limited to, hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, laurylsulphonate salts, hydroxide, carbonate, ammonia salts, organic primary, secondary or tertiary amine salts, lithium, sodium, potassium, calcium, magnesium, aluminum salts, ethylamine, diethylamine, ethylenediamine, ethanolamine, diethanolamine, and piperazine.

In yet another embodiment, the invention also pertains, at least in part, to methods for determining an advantageous prodrug form of an agent. The methods include obtaining a first small molecule profile of a sample from a subject treated with a first prodrug form of the agent; obtaining a second small molecule profile of a sample from a second subject treated with a second prodrug form of the agent; comparing the first small molecule profile to the second small molecule profile; identifying components of the small molecule profiles affected by the prodrug form of the agent; identifying biochemical pathways associated with the components; and using the identified biochemical pathways to identify an advantageous prodrug form. The first and second subjects may be the same or different.

The term "advantageous prodrug forms" includes prodrugs forms which, for example, are selected to minimize negative unexpected effects of the agent and/or maximize therapeutic effects of the agent. Examples of types of moieties that can be used as prodrugs include, but are not limited to, substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides.

In yet another embodiment, the invention also pertains, at least in part, to methods for determining an advantageous route of administration of an agent. The methods include: obtaining a first small molecule profile of a sample from a first subject treated with an agent administered using a first route of administration; obtaining a second small molecule profile of a sample from a second subject treated with the agent administered using a second route of administration; comparing the first small molecule profile to the second small molecule profile; identifying components of the small molecule profiles affected by the route of administration of the agent; identifying biochemical pathways associated with the components; and using the identified biochemical pathways to identify an advantageous route of administration. The first and second subjects may be the same or different. The agent may be administered in combination with a pharmaceutically acceptable carrier, advantageously compatible with the route of administration.

Examples of "routes of administration" include but are not limited to oral, nasal, topical, transdermal, buccal, sublingual, rectal, vaginal and parenteral administration.

In another embodiment, the invention also pertains, at least in part, to methods for determining an advantageous formulation of an agent. The methods include obtaining a first small molecule profile of a sample from a first subject treated with a first formulation of the agent; obtaining a second small molecule profile of a sample from a second subject treated with a second formulations of the agent; comparing the first small molecule profile to the second small molecule profile; identifying components of the small molecule profiles affected by the formulation of the agent; identifying biochemical pathways associated with the components; and using the identified biochemical pathways to identify an advantageous formulation.

Examples of "formulations" include, but are not limited to, preparations which can be used for oral, nasal, topical, transdermal, buccal, sublingual, rectal, vaginal and parenteral administration. In a further embodiment, the formulation is a tablet which may be administered orally. The formulations may advantageously comprise pharmaceutically acceptable carrier.

When administered to a living subject, such as a human, it may be advantageous to administer the agent in combination with a pharmaceutically effective carrier. The methods of the invention may also be used to determine the most effective (e.g., fewest negative unexpected effects, fewest off target effects, most therapeutic effects, most on target effects, most agent delivered to tissues intended to be treated, etc.) method of administering a particular agent to a subject.

The phrase "pharmaceutically acceptable carrier" is art recognized and includes a pharmaceutically acceptable material, composition or vehicle, suitable for administering an agent to subjects. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the subject. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations include those suitable for oral, nasal, topical, transdermal, buccal, sublingual, rectal, vaginal and/or parenteral administration. The formulations may be prepared by any methods well known in the art of pharmacy.

Methods of preparing these formulations or compositions include the step of bringing into association a compound of the present invention with the carrier and, optionally, one or more accessory ingredients. In general, the formulations are prepared by uniformly and intimately bringing into association an agent with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent. The agents may also be administered as a bolus, electuary or paste.

In solid dosage forms of the invention for oral administration (capsules, tablets, pills, dragees, powders, granules and the like), the agent is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the agent, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The agent can also be in micro-encapsulated form, if appropriate, with one or more of the above-described excipients.

Liquid dosage forms for oral administration of the agents include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical formulations for rectal or vaginal administration may be presented as a suppository, which may be prepared by mixing one or more agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of an agent to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions suitable for parenteral administration comprise one or more agents (preferably, one agent) in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of an agent, it may be desirable to slow the absorption of the agent from subcutaneous or intramuscular injection. This may be accomplished by the use of a liquid suspension of crystalline or amorphous material having poor water solubility. The rate of absorption of the agent then depends upon its rate of dissolution which, in turn, may depend upon crystal size and crystalline form. Alternatively, delayed absorption of a parenterally-administered agent is accomplished by dissolving or suspending the agent in an oil vehicle.

Injectable depot forms are made by forming microencapsule matrices of the agents in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly (anhydrides). Depot injectable formulations are also prepared by entrapping the drug in liposomes or microemulsions which are compatible with body tissue.

The preparations described herein may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. The methods of the invention can be used to determine the most effective methods of administering the agents and the most effective methods of formulating the agents to be administered.

The phrases "parenteral administration" and "administered parenterally" include modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" include the administration of an agent other than directly into the central nervous system, such that it enters the patient's system and, thus, is subject to metabolism and other like processes, for example, subcutaneous administration.

The agents may be administered to subjects by any route of administration, including orally, nasally, as by, for example, a spray, rectally, intravaginally, parenterally, intracisternally and topically, as by powders, ointments or drops, including buccally and sublingually.

The invention also includes automated and/or semiautomated methods, computer programs, and other related mediums for performing the methods of the invention.

FIG. 1 depicts an environment suitable for practicing an embodiment of the present invention. A computing device 2 holds or enables access to a collection of data describing biochemical pathways 4. The computing device 2 may be a server, workstation, laptop, personal computer, PDA or other computing device equipped with one or more processors and able to execute the analysis facility 6 discussed herein. The collection of data describing biochemical pathways 4 may be stored in a database. The collection of data describing biochemical pathways 4 describes multiple biochemical pathways with each biochemical pathway description identifying multiple compounds associated with a particular biochemical pathway. The analysis facility 6 is preferably implemented in software although in an alternate implementation, the logic may be also be implemented in hardware. The analysis facility 6 operates on and analyzes results data 22 received from a data acquisition apparatus 20. As will be explained further below, the results data 22 indicates a condition of a compound in an assay 30 that is being processed by the data acquisition apparatus 20 to which an agent has been added.

The assay to which the agent may be added 30 may be an in vitro assay or an in vivo assay, as described above. The data acquisition apparatus 20 processes an assay following the addition of an agent to the assay in order to determine the effect or non-effect of the agent on the assay. The processing of the assay with the agent by the data acquisition apparatus 20 may take place using gas chromatography-mass spectrometry (GC-MS), liquid chromatography, gas chromatography, mass spectrometry, liquid chromatography-mass spectrometry (LC-MS) or other techniques able to analyze the effect of the addition of the agent to the assay, as described above. The processing of the assay with the agent 30 by the data acquisition apparatus 20 generates results data 22 that indicates a condition of at least one compound (e.g., a small molecule profile) in the assay relative to a control (e.g., standard small molecule profile). The indicated condition may reflect a change in the compound (and associated biochemical pathway(s)) as a result of the addition of the agent 30 to the assay. Alternatively, the indicated condition of the compound may reflect that the compound has not changed as a result of the addition of the agent 30 to the assay. It will be appreciated that the lack of a change in the compound may represent an expected and/or desired result depending upon the identity of the agent and assay. The results data 22 is provided to the analysis facility 6 executing on the computing device 2. As will be appreciated, there are a number of ways in which the results data may be transmitted to the computing device 2 including, but not limited to, the use of a direct or networked connection between the data acquisition apparatus 20 and the computing device 2 or by saving the results data to a storage medium such as a compact disc that is then transferred to the computing device 2. For ease of illustration, FIG. 1 depicts a direct connection between the data acquisition apparatus 20 and the computing device 2 over which the results data 22 may be conveyed. Those skilled in the art will recognize that many other configurations are also possible within the scope of the present invention.

The analysis facility 6 uses the results data indicating a condition of one or more compounds 22 together with the collection of data describing biochemical pathways 4 to identify one or more biochemical pathways affected by the addition of the agent to the assay 30. A beneficial aspect of this technique is that it enables the effect of an agent to be studied on a broad range of biochemical pathways rather than just a narrowly targeted study as is done with conventional techniques. This allows both expected and unexpected effects of an agent as well as lead candidates to be identified much earlier in the drug development process. As will be appreciated, the identification of lead candidates or negative effects earlier in the drug development process can result in substantial monetary and time savings to the entities attempting to identify lead candidates.

In one implementation, the comparison of the results data 22 to the collection of biochemical pathways 4 in order to identify the affected biochemical pathways is performed programmatically without any user input. In alternate implementations, the analysis facility 6 prompts a user for parameters for the comparison. The parameters may limit for example, the number of compounds indicated in the results data 22 that are to be compared with the collection of data describing biochemical pathways 4. Alternatively, the parameters solicited from a user by the analysis facility 6 may limit the amount of the collection of data describing biochemical pathways 4 that is searched. Additional types of user input and parameters that may be solicited from the user by the analysis facility 6 will occur to those skilled in the art and are considered to be within the scope of the present invention.

As noted above, the analysis facility 6 uses the results data indicating a condition of one or more compounds 22 together with the collection of data describing biochemical pathways 4 to identify one or more biochemical pathways affected by the addition of the agent to the assay 30. A listing of the identified biochemical pathways 42 may be transmitted to, and displayed on, a display device 40 in communication with the computing device 2. As will be discussed further below, the listing of the identified biochemical pathways 42 may also list details of changes in metabolites 42 in the identified biochemical pathways 40. Alternatively, a listing of the identified biochemical pathways 12 may be stored in storage 10 for later analysis or presentment to a user. For ease of illustration, storage 10 is depicted as being located on the computing device 2 in FIG. 1. It will be appreciated that storage 10 could also be located at other locations accessible to computing device 2.

The analysis facility 6 may also include, or have access to, pre-defined criteria 8 which is used to interpret the meaning of the identified condition of the affected biochemical pathways. In one implementation, the pre-defined criteria may be used to programmatically provide an interpretation without user input. In other implementations, varying degrees of user input in addition to a programmatic application of the pre-defined criteria may be used to interpret the meaning of an identified change in biochemical pathways. In still other implementations, the interpretation may be wholly provided by a user presented with a listing of the identified biochemical pathways by the analysis facility 6. As discussed further in reference to FIG. 4 below, the interpretation may provide information on the significance of identified metabolite or small molecule changes in the biochemical pathways. The pre-defined criteria may be held in a database accessible to the analysis facility 6.

Figure 2:
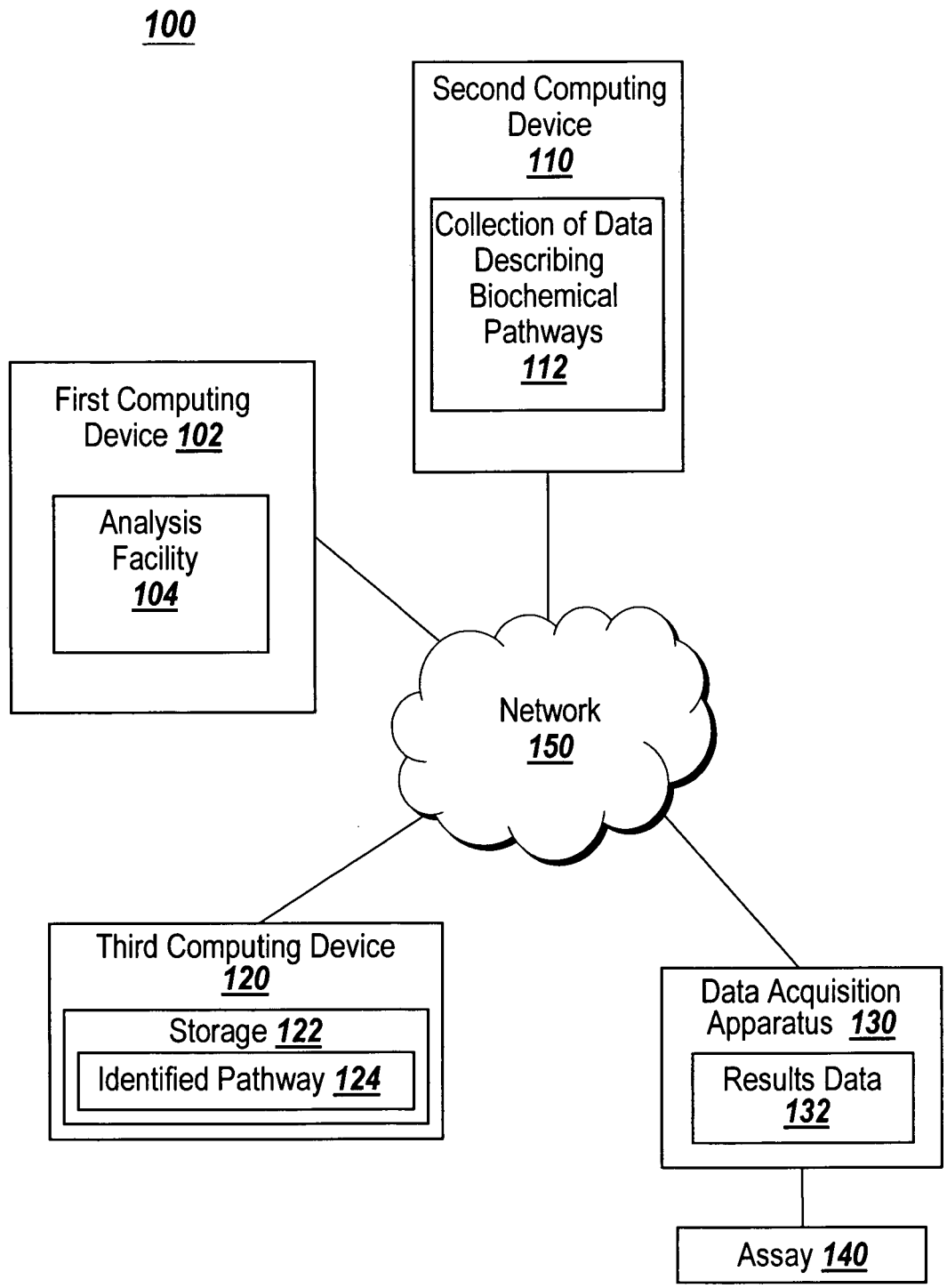
FIG. 2 depicts an alternative distributed environment suitable for practicing an embodiment of the present invention.

FIG. 2 depicts an alternative distributed environment suitable for practicing an embodiment of the present invention. A first computing device 102 may be used to execute an analysis facility 104. The first computing device may communicate over a network 150 with a second computing device 110 holding a collection of data describing biochemical pathways 112. The network 150 may be the Internet, a local area network (LAN), a wide area network (WAN), an intranet, an internet, a wireless network or some other type of network over which the first computing device 102 and the second computing device 110 can communicate. The analysis facility 104 on the first computing device 102 may communicate over the network 150 with a data acquisition apparatus 130 generating results data 132 from the processing of an assay with an agent 140. The analysis facility 104 may store a listing of identified biochemical pathways 124 affected by the addition of the agent to the assay that is obtained by processing the results data 132 and the collection of data describing biochemical pathways 112 in storage 122. Storage 122 may be located on a third computing device 120 accessible over the network 150. It should be recognized that FIG. 2 depicts only a single distributed configuration and many other distributed configurations are possible within the scope of the present invention.

Figure 3:
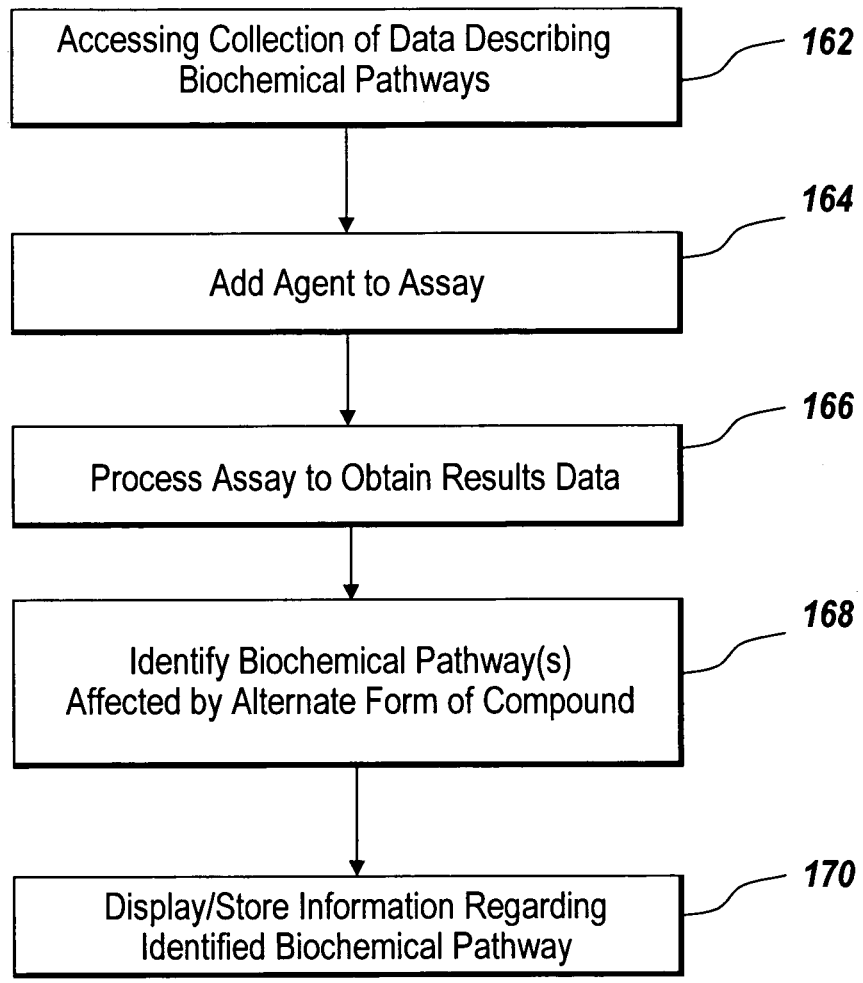
FIG. 3 is a flowchart of a sequence of steps that may be followed by an illustrative embodiment of the present invention to identify biochemical pathways affected by the addition of an agent to an assay.

FIG. 3 is a flowchart of a sequence of steps that may be followed by an embodiment of the present invention to identify biochemical pathways affected by alternate forms of the agent. The sequence begins by accessing a collection of data describing biochemical pathways (step 162). An agent is then added to an assay (step 164) and the assay is processed by a data acquisition apparatus to obtain results data (step 166) as discussed above. The results data and the collection of data describing biochemical pathways is then used by the analysis facility to identify biochemical pathways affected by the addition of the agent to the assay (step 168). A listing of the affected biochemical pathways may then be displayed to a user or stored for later retrieval (step 170). It will be appreciated that in an alternative implementation the accessing of the collection of data describing biochemical pathways may not take place until after the addition of the agent to the assay.

One beneficial aspect of the present invention is the ability of the analysis facility to generate a concise report indicating the affects associated with the agent being studied. FIG. 4 is an exemplary concise report 200 that may be produced by the analysis facility to display metabolite data for biochemical pathways identified as affected by the addition of the agent to an assay. The concise report 200 includes a title 202 indicating a compound being studied. The concise report also includes a listing of the biochemical pathways 210 affected by the addition of the agent to an assay. Additional columns 212 and 214 corresponding to alternate dosages may also be provided. For example, a column including results for a high dose versus a control 212 and a medium dose versus a control 214 may be provided. The results data in the columns may list any metabolite changes within the affected biochemical pathways. In one implementation, a visual indicator may be provided for a user to indicate the type of metabolite change. For example, one color may be used to indicate an increase in a metabolite level for a particular biochemical pathway while a second color may be used to indicate a decrease in a metabolite level for the particular biochemical pathway. Similarly, other types of visual indicators may be used in place of, or in addition to color, to convey information to a user. The use of a visual indicator is an additional benefit of the present invention in that it facilitates quick recognition of an overall effect for an agent. For example, if the color red is being used to indicate an increase in metabolite (or small molecule) levels in biochemical pathways and an agent causes widespread increases in metabolite levels, a user glancing quickly at the concise report will be able to quickly ascertain the effect of the agent. For cases where there are a lot of affected biochemical pathways affected by the agent being studied and a corresponding large amount of information being conveyed in the report, the visual indicator thus provides an efficient mechanism for conveying information.

The concise report 200 may also include a footnote column 216 referencing portions of an interpretation 220 discussing the meaning of the identified changes in metabolite levels in the various biochemical pathways. The interpretation 220 may be generated programmatically by the analysis facility, may be supplied manually by a user looking at the rest of the concise report 200, or may be a hybrid that is produced in part by the analysis facility and in part by a user.

The present invention may be provided as one or more computer-readable programs embodied on or in one or more mediums. The mediums may be a floppy disk, a hard disk, a compact disc, a digital versatile disc, a flash memory card, a PROM, a RAM, a ROM, or a magnetic tape. In general, the computer-readable programs may be implemented in any programming language. Some examples of languages that can be used include FORTRAN, C, C++, C#, or JAVA. The software programs may be stored on or in one or more mediums as object code. Hardware acceleration may be used and all or a portion of the code may run on a FPGA or an ASIC. The code may run in a virtualized environment such as in a virtual machine. Multiple virtual machines running the code may be resident on a single processor. The code may be run using more than one processor having two or more cores each.

Since certain changes may be made without departing from the scope of the present invention, it is intended that all matter contained in the above description or shown in the accompanying drawings be interpreted as illustrative and not in a literal sense. Practitioners of the art will realize that the sequence of steps and architectures depicted in the figures may be altered without departing from the scope of the present invention and that the illustrations contained herein are singular examples of a multitude of possible depictions of the present invention.

Exemplification of the Invention

Example 1

Rosiglitazone Maleate Treatment of Adipocytes

Adiopocyte cells were treated with 0-low-high concentrations of rosiglitazone maleate (Table 1). Cells were harvested after treatment and submitted to the metabolomic platform for analysis. Following data curation, the results were statistically analyzed and the compounds that were statistically significantly increased or decreased in response to rosiglitazone maleate relative to the control cells (i.e. cells treated with vehicle only) were identified. These compounds were mapped to biochemical pathways as shown in Table 2 and the effects of changes in these biochemical pathways on the biology of the cell were determined. The biological interpretation of the biochemical profile results is summarized in Table 2.

TABLE 1

| Rosiglitazone maleate | Number |
|---|---|
| Vehicle only (Control) | 8 |
| High dose | 8 |
| Low dose | 8 |

TABLE 2

| Kegg Pathway (& denotes Super Pathways) | Specific Metabolites changed/pathway (high vs 0 dose, q < 0.2) | Specific Metabolites changed/pathway (medium vs 0 dose, q < 0.2) | Summary Ref.# |
|---|---|---|---|
| Alanine and aspartate metabolism & Selenoamino acid metabolism | Alanine<br>Aspartate<br>β-ala | Aspartate | 2 |
| Aminosugars metabolism | UDP-N-acetylgalactosamine | | |
| beta-Alanine metabolism | Asp<br>β-ala | Asp | 2 |
| Biosynthesis of steroids & C21-Steroid hormone metabolism & Bile acid biosynthesis & Hedgehog signaling pathway | Chol<br>3HMG*<br>Gly | Chol | 3 |
| Citrate cycle (TCA cycle) & Reductive carboxylate cycle ($CO_2$ fixation) & Glyoxylate and dicarboxylate metabolism | Malate<br>Succinate<br>Citrate | Malate<br>Succinate | |
| Cyanoamino acid metabolism & Cysteine metabolism & Sphingolipid metabolism & Methane metabolism | Gly<br>Ser | | 2 |
| Fructose and mannose metabolism | G6P | G6P | 5 |
| Galactose metabolism | Glycerol<br>Lactose | Glycerol<br>Lactose | |
| Glutamate metabolism & D-Glutamine and D-glutamate metabolism | Succinate<br>Phe<br>Gln<br>Tyr<br>γ-glu-cys<br>γ-Glu-gln* | Succinate<br>Phe | 2 |
| Glutathione metabolism | 5-oxopro<br>Gly<br>Tyr<br>γ-glu-cys | 5-oxopro | 1 |
| Glycerolipid metabolism | Glycerol | Glycerol | 4 |
| Glycine, serine and threonine metabolism & Lysine degradation | Ser<br>Gly<br>Thr | | 2 |
| Glycolysis/Gluconeogenesis | Lactate | | |
| Histidine metabolism | Tyr<br>Asp<br>His | Asp<br>His | 2 |
| Methionine metabolism | Met<br>SAH<br>Ser | Met<br>SAH | 2 |
| Nicotinate and nicotinamide metabolism | Niacinamide | Niacinamide | |
| Oxidative phosphorylation | Succinate<br>Phosphate | Succinate<br>Phosphate | |
| Pantothenate and CoA biosynthesis | Val<br>β-ala | Val (slt) | 2 |

TABLE 2-continued

| Kegg Pathway (& denotes Super Pathways) | Specific Metabolites changed/pathway (high vs 0 dose, q < 0.2) | Specific Metabolites changed/pathway (medium vs 0 dose, q < 0.2) | Summary Ref.# |
|---|---|---|---|
| Pentose Phosphate Pathway & Pentose and glucuronate interconversions | Phosphate Ribulose-5-phosphate 6-phosphogluconate | Phosphate Ribulose-5-phosphate | 5 |
| Phenylalanine metabolism | 6-phosphogluconate | 6-phosphogluconate | |
| Phenylalanine, tyrosine and tryptophan biosynthesis & Tyrosine metabolism | Trp | Trp 6-phosphogluconate | |
| Propanoate metabolism | Succinate β-ala | Succinate | |
| Purine metabolism | Phe Gln Guanosine Guanine 2'-deoxyguanosine Urea Adenosine Inosine | Phe Gln Guanosine Guanine 2'-deoxyguanosine Urea | 2 |
| Pyrimidine metabolism | Phe Hypoxanthine UMP (slt) β-ala CMP Gln | Phe Hypoxanthine UMP | 2 |
| Pyruvate metabolism | Malate Lactate | Malate | |
| Starch and sucrose metabolism | Uridine | Uridine | |
| Tryptophan metabolism | Maltose | Maltose | |
| Urea cycle and metabolism of amino groups & Arginine and proline metabolism | Pro Glu Asp Ornithine Putrescine (slt) Urea N(5)-(aminocarbonyl)-L-ornithine Creatinine (slt)* Tyr | Pro Glu Asp Ornithine Putrescine Urea | 3 |
| Valine, leucine and isoleucine degradation | Leu Ile Val | Val (slt) | 2 |
| No Map | α-L-Sorbopyranose N-gly-val N-acetyl-D-galactosamine | α-L-Sorbopyranose N-gly-val N-acetyl-D-galactosamine Creatinine γ-Glu-gln | |

5-oxoproline is generated via oxoprolinase (rate-limiting) in the g-glutamyl cycle 1. Increased 5-oxoproline resulted from increased g-glu-cys, due to low activity of glutathione synthase. Decreased g-glutamy cycle activity could limit transport of AA against a gradient, affecting AA levels 2. Increases in various AA is also likely related to increased protein turn over. Consistent with increased generation of AA, urea cycle intermdiates and polyamines were increased 3. Typically, rosiglitazone increases cholesterol in cultured adipocytes by increasing uptake of cholesterol from the media via activation of scavenger receptors (e.g., oxidized LDL receptor 1). Cholesterol decreased, and this could be related to a lack of cholesterol provided in the media 3. The decrease in glycerol is consistent with rosiglitazone-induced increases in glycerol kinase 4. Typically, rosiglitazone increases free fatty acids (FFA) in adipocytes, and these FFA are rapidly stored as triacylglycerols (TAG). Our current system does not detect intact TAG. The increase in G6P, and decrease in 6-phosphogluconate and ribulose 5-P, suggests decreased flux through the pentose phosphate pathway.

Example 2

A Comparative Metabolomic Analysis of PPAR Activators

In this example, five PPAR activators were tested. These activators were selective to either PPAR gamma, PPAR delta, and PPAR alpha. In addition, five other PPAR compounds (including troglitazone which was removed from the market because of liver safety concerns) were compared as well.

The cell used in this assay were preadipocyte cells from a 37 year old female human with a BMI of 23.29. The cells were plated at 1 million per well in 6-well plates. Eight cultures were used for each experimental group. The cells were washed with basal medium (1 ml/well) and treated with compounds in 1 ml of basal medium for 3 hours. After treatment, the cells were then washed with PBS (1 ml), two times and then trypsinized with 300 μl for 5 minutes at 37 degrees. One ml of PM-1 was then added per well to neutralized the trypsin and the cells were collected in 1.5 ml eppendorf tube. The cells were then pelleted by centrifugation (280×g) and the pellets were washed with PBS (1 ml). The cell pellets were then frozen at −80 degrees.

Figure 5:
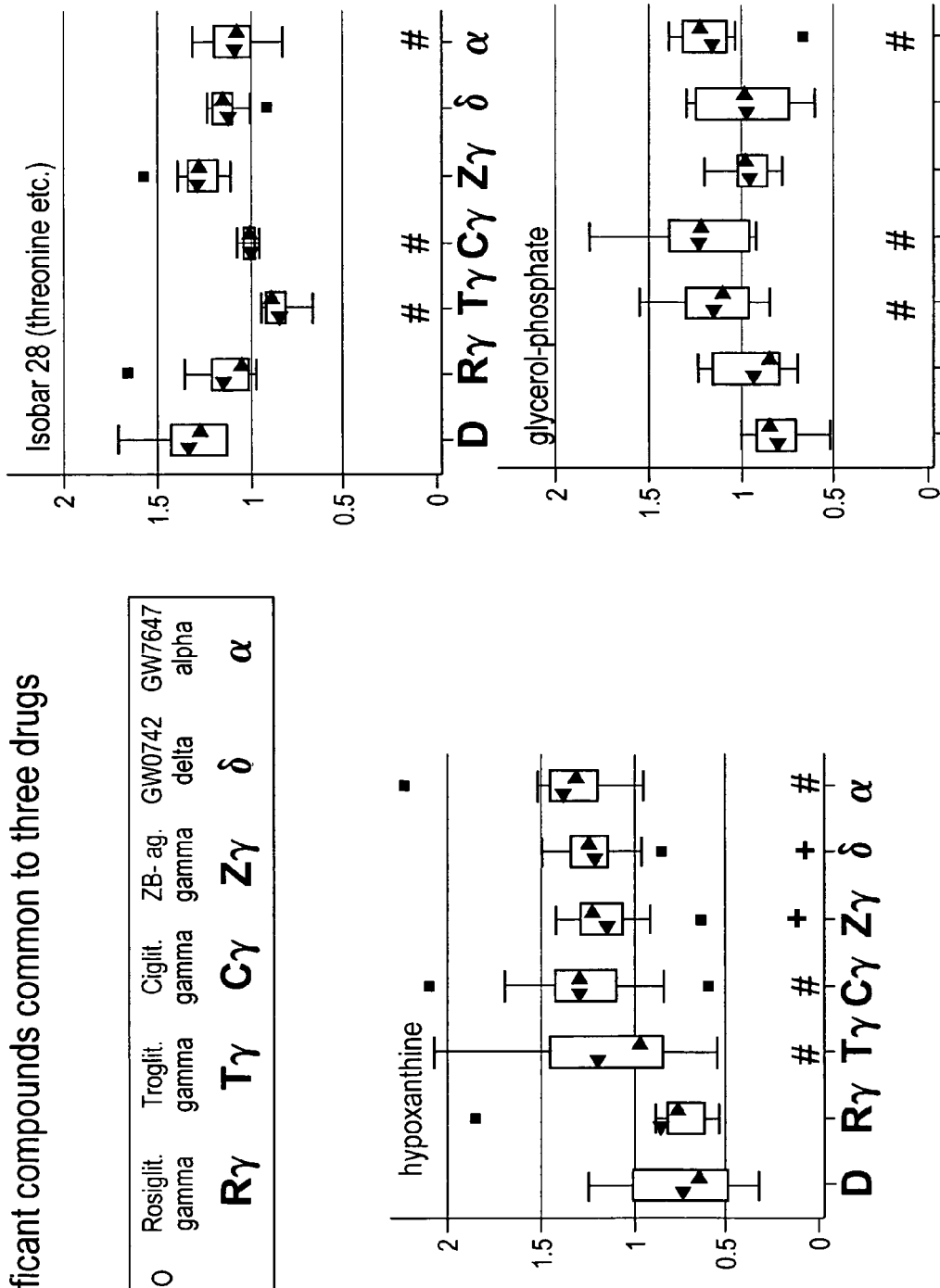
FIG. 5 shows three bar graphs which show the concentrations of significant compounds common to three of the drugs tested.
Figure 6:
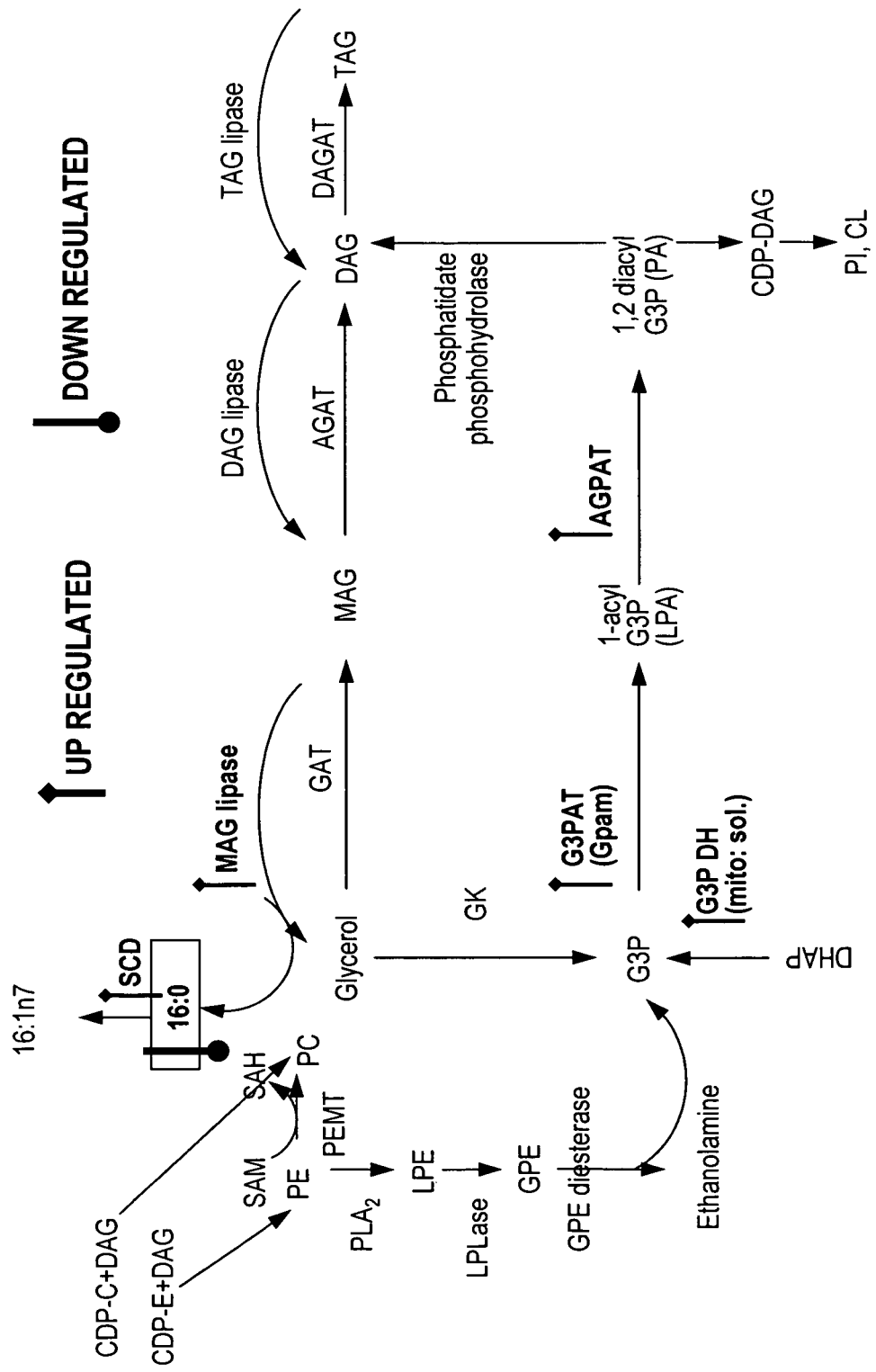
FIG. 6 shows a biological pathway illustrating the effect of compounds on glycerol-3-phosphate biochemistry.

The results are summarized in FIGS. 5-10 and in Tables 3-5. FIG. 5 shows the affect of the drugs on three compounds common to at least three drugs. FIG. 5A shows the results for hypoxanthine, FIG. 5B shows the results for Isobar 28 (threonine, etc.) and FIG. 5C shows the effects of the compounds on the glycerol phosphate levels. This data is further described in Table 3.

TABLE 3

| COMPOUND | Trog vs. DMSO pvalue | Cigl vs. DMSO pvalue | GW7647 vs. DMSO pvalue | Ratio Drug/DMSO | | |
|---|---|---|---|---|---|---|
| | | | | Troglitazone | Ciglitazone | GW7647 |
| Isobar-28-includes-L-threonine-L-allothreonine-L-homoserine | 2.21E−07 | 6.20E−05 | 0.0104 | 0.63 | 0.72 | 0.82 |
| sn-glycerol-3-phosphate | 0.0045 | 0.0009 | 0.0041 | 1.42 | 1.53 | 1.43 |
| hypoxanthine | 0.0100 | 0.0017 | 0.0003 | 1.63 | 1.76 | 1.89 |

Not to be limited by theory, the levels of glycerol-3-phosphate (G3P) changes because PPARα and -γ agonists affect transcription of enzymes responsible for its synthesis (via G3PDH) and conversion to other substrates (via G3PAT & AGPAT). This process is described in FIG. 6.

Table 4, below, shows compounds which were identified comparing the small molecule profiles of the assay treated with Troglitazone with the assay treated with Cigilitazone. Both the small molecule profile are relative to a DMSO control. Table 4 shows significant increases in the concentration of aspartate, sn-glycerol-3-phosphate, hypoxanthine, and o-phosphoethanolamine.

ways. For example when troglitazone is added to the assay, increases in n-hexadecanoic acid (palmitate) and octadecanoic acid (stearate) are perhaps due to adipogenesis and lipid accumulation. Furthermore, decreases in acetyl N-acetyl ornithine are perhaps due to shunting Orn to Putrescine, thus resulting in less Orn available for N-Ac Orn production, which is known to be activated by PPARγ. Inosine is a marker of energy depletion and is thus increased by PPAR agonist which induce mitochondrial uncoupling. Furthermore, carnitine palmitoyl transferase (CPTI) is a PPARα target whose activation contributes to increased b-oxidation following treatment with GW7647. As β-oxida-

TABLE 4

| COMPOUND | Trog vs. DMSO pvalue | Cigl vs. DMSO pvalue | Ratio Drug/DMSO | |
|---|---|---|---|---|
| | | | Troglitazone | Ciglitazone |
| aspartate | 7.77E−16 | 0.0002 | 2.06 | 1.29 |
| Isobar-28-includes-L threonine-L-allothreonine-L-homoserine | 2.21E−07 | 6.20E−05 | 0.63 | 0.72 |
| ** oxidized-glutathione | 0.0002 | 0.0003 | 0.77 | 0.77 |
| threonine | 0.0003 | 0.0006 | 0.83 | 0.84 |
| glutamine | 0.0009 | 0.0031 | 0.76 | 0.78 |
| gamma-L-glutamyl-L-glutamin | 0.0016 | 0.0176 | 0.64 | 0.73 |
| sn-glycerol-3-phosphate | 0.0045 | 0.0009 | 1.42 | 1.53 |
| hypoxanthine | 0.0100 | 0.0017 | 1.63 | 1.76 |
| o-phosphoethanolamine | 0.0157 | 1.19E−13 | 1.50 | 5.42 |

Table 5 shows that each of troglitazone, cigilitazone, and GW7647 effected certain compounds in their respectively small molecule profile differently. These individual changes in small molecule profiles are likely to be the result of their unique interactions with the assays and the biological pathways. tion is increased, more carnitine is being utilized to shuffle FA into the mitochondria and hence, levels decrease. In addition, the increase in glycerol with GW7647 is related to PPARα activation of MAG lipase. The results are further summarized in Table 5.

TABLE 5

| COMPOUND | Trog vs. DMSO pvalue | Cigl vs. DMSO pvalue | GW7647 vs. DMSO pvalue | Ratio Drug/DMSO | | |
|---|---|---|---|---|---|---|
| | | | | Troglitazone | Ciglitazone | GW7647 |
| pantothenic acid | 3.37E−06 | 0.0894 | 0.4137 | 1.33 | 1.10 | 0.96 |
| serine | 0.0011 | 0.6662 | 0.2087 | 0.86 | 0.98 | 1.05 |
| 3-phospho-l-serine | 0.0011 | 0.2456 | 0.0985 | 0.77 | 0.91 | 0.89 |
| alanine | 0.0027 | 0.0495 | 0.3335 | 0.86 | 0.91 | 0.95 |
| n-hexadecanoic acid | 0.0095 | 0.4268 | 0.7323 | 1.17 | 1.05 | 1.02 |
| octadecanoic acid | 0.0121 | 0.5435 | 0.7525 | 1.18 | 1.05 | 1.02 |
| Isobar-17-includes-arginine-N-alpha-acetyl-ornithine | 0.0134 | 0.0428 | 0.6642 | 0.82 | 0.87 | 0.97 |
| gly-gly | 0.0145 | 0.0300 | 0.4114 | 1.42 | 1.36 | 1.12 |
| citric acid | 0.0163 | 0.1093 | 0.5597 | 0.77 | 0.86 | 1.06 |
| N-acetyl-D-galactosamine | 0.2709 | 3.03E−14 | 0.8809 | 0.91 | 0.36 | 0.98 |
| guanosine | 0.5124 | 0.0011 | 0.1480 | 0.98 | 1.55 | 1.22 |
| inosine | 0.2348 | 0.0061 | 0.0176 | 1.58 | 2.25 | 1.89 |
| phosphoenolpyruvate | 0.1391 | 0.0139 | 0.4815 | 0.85 | 0.76 | 0.91 |
| tryptophan | 0.5267 | 0.0220 | 0.1339 | 0.98 | 0.91 | 1.06 |
| L-alpha-glycerophosphorylcholine | 0.2427 | 0.0248 | 0.1693 | 1.24 | 1.81 | 1.31 |

TABLE 5-continued

| COMPOUND | Trog vs. DMSO pvalue | Cigl vs. DMSO pvalue | GW7647 vs. DMSO pvalue | Ratio Drug/DMSO | | |
|---|---|---|---|---|---|---|
| | | | | Troglitazone | Ciglitazone | GW7647 |
| carnitine | 0.1484 | 0.0764 | 0.0016 | 0.92 | 0.90 | 0.83 |
| Isobar-22-includes-glutamic acid-O-acetyl-L-serine | 0.1155 | 0.8514 | 0.0041 | 0.92 | 0.99 | 0.86 |
| glycerol | 0.0657 | 0.1216 | 0.0049 | 1.08 | 0.93 | 1.14 |
| adenosine-5-monophosphate | 0.4083 | 0.5183 | 0.0066 | 0.95 | 1.09 | 1.41 |

Figure 7:
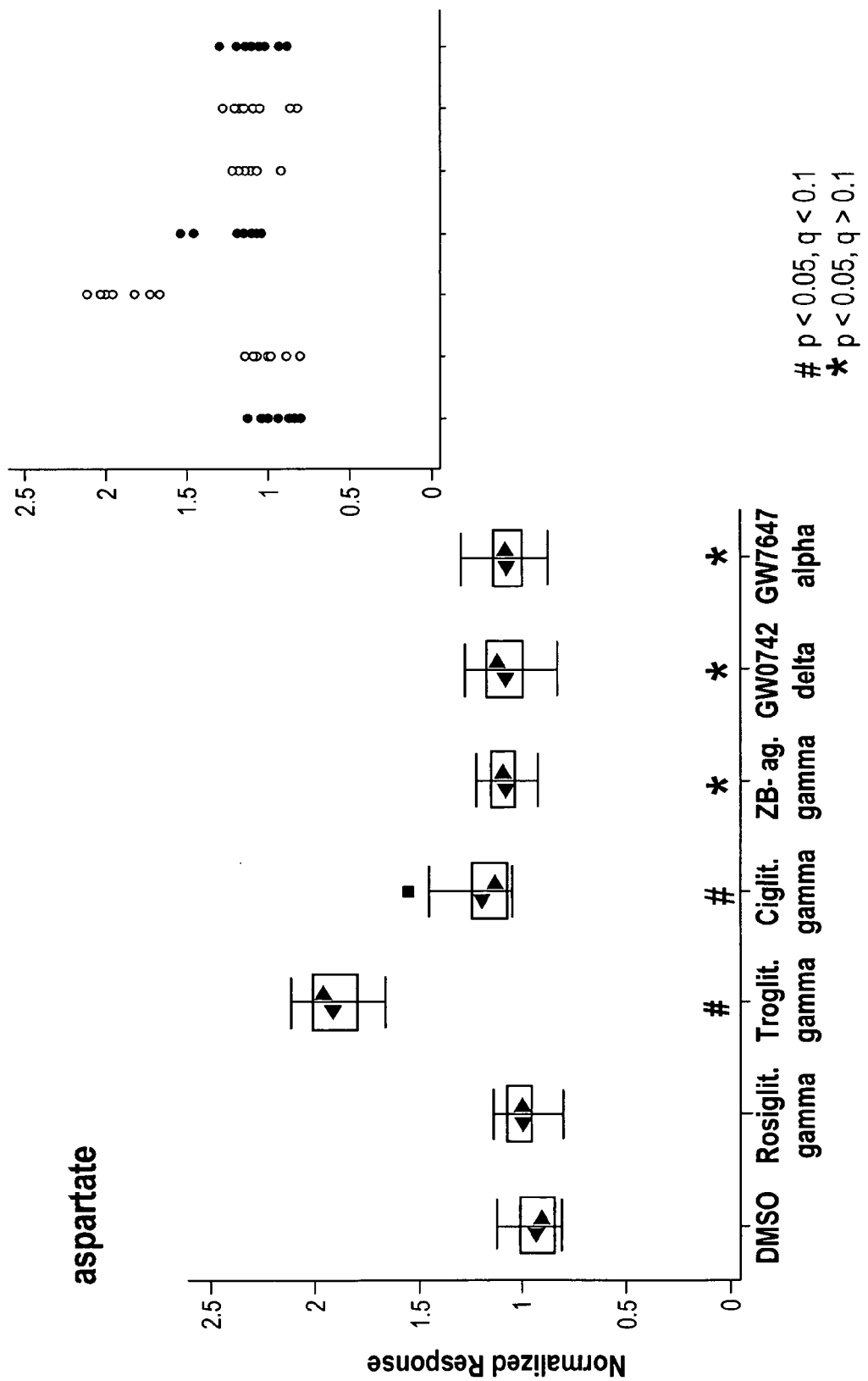
FIG. 7 is a graph which shows comparative levels of aspartate for six drugs.
Figure 8:
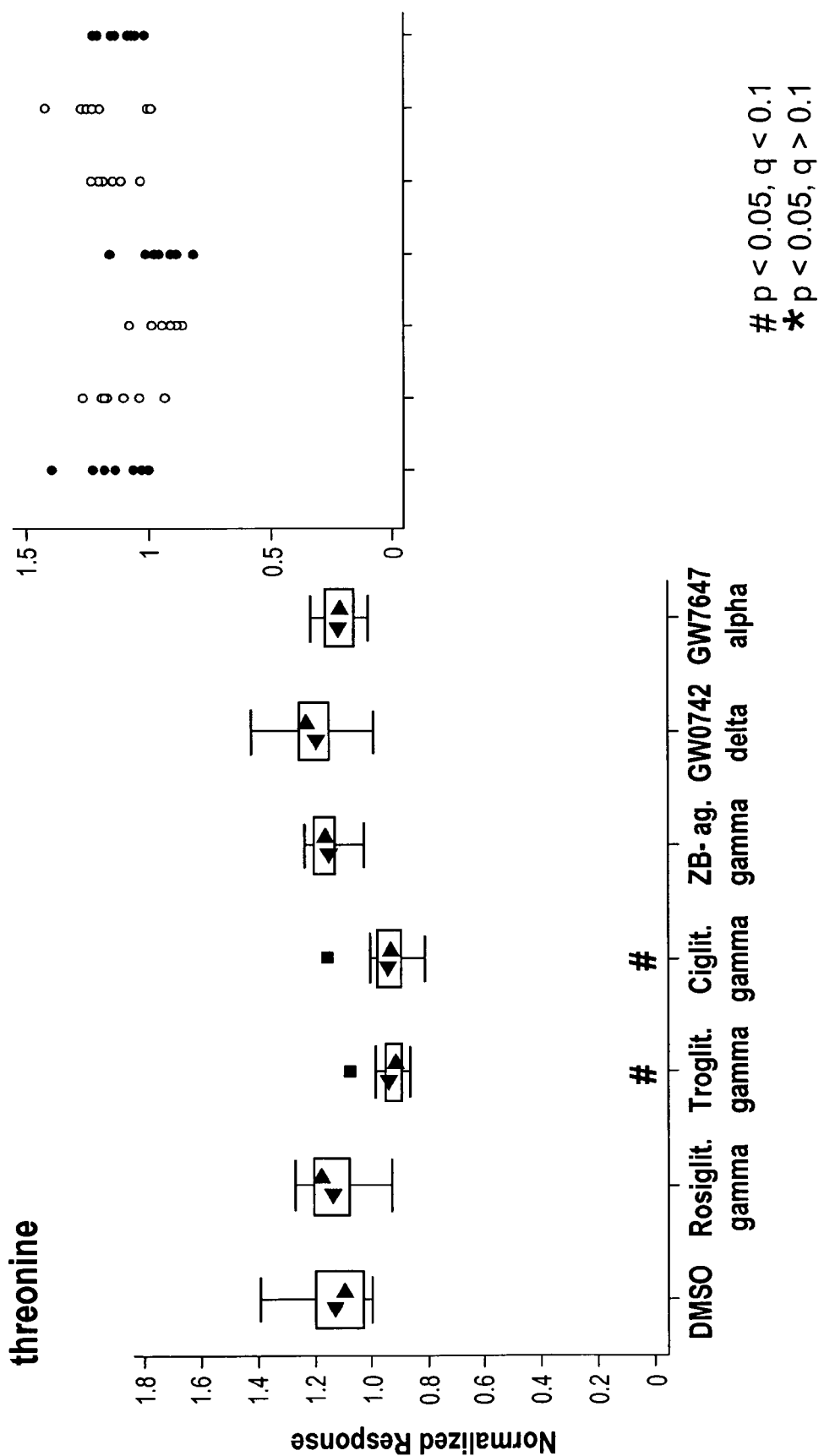
FIG. 8 is a graph which shows comparative levels of threonine for six drugs.
Figure 9:
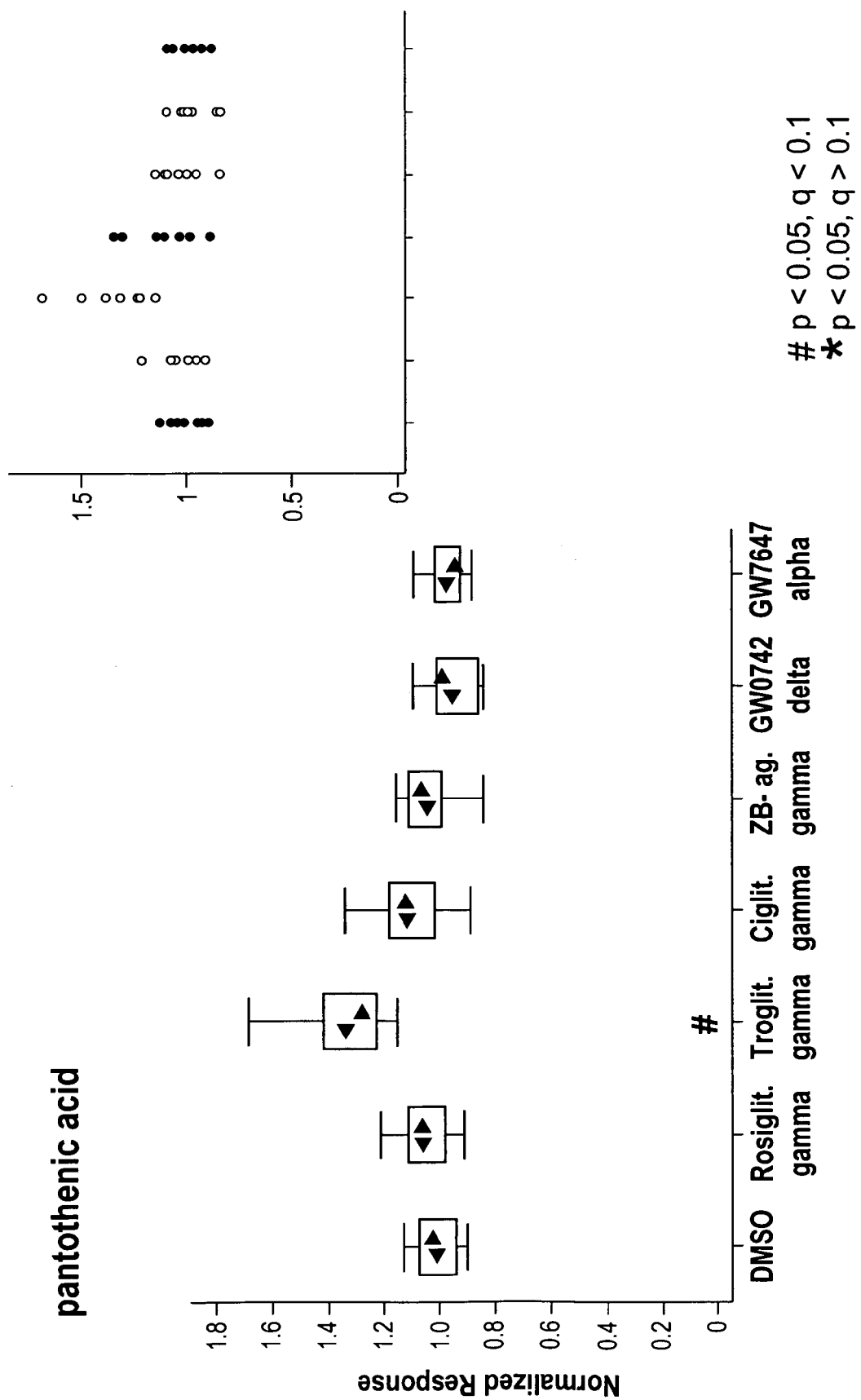
FIG. 9 is a graph which shows comparative levels of pantothenic acid for six drugs.
Figure 10:
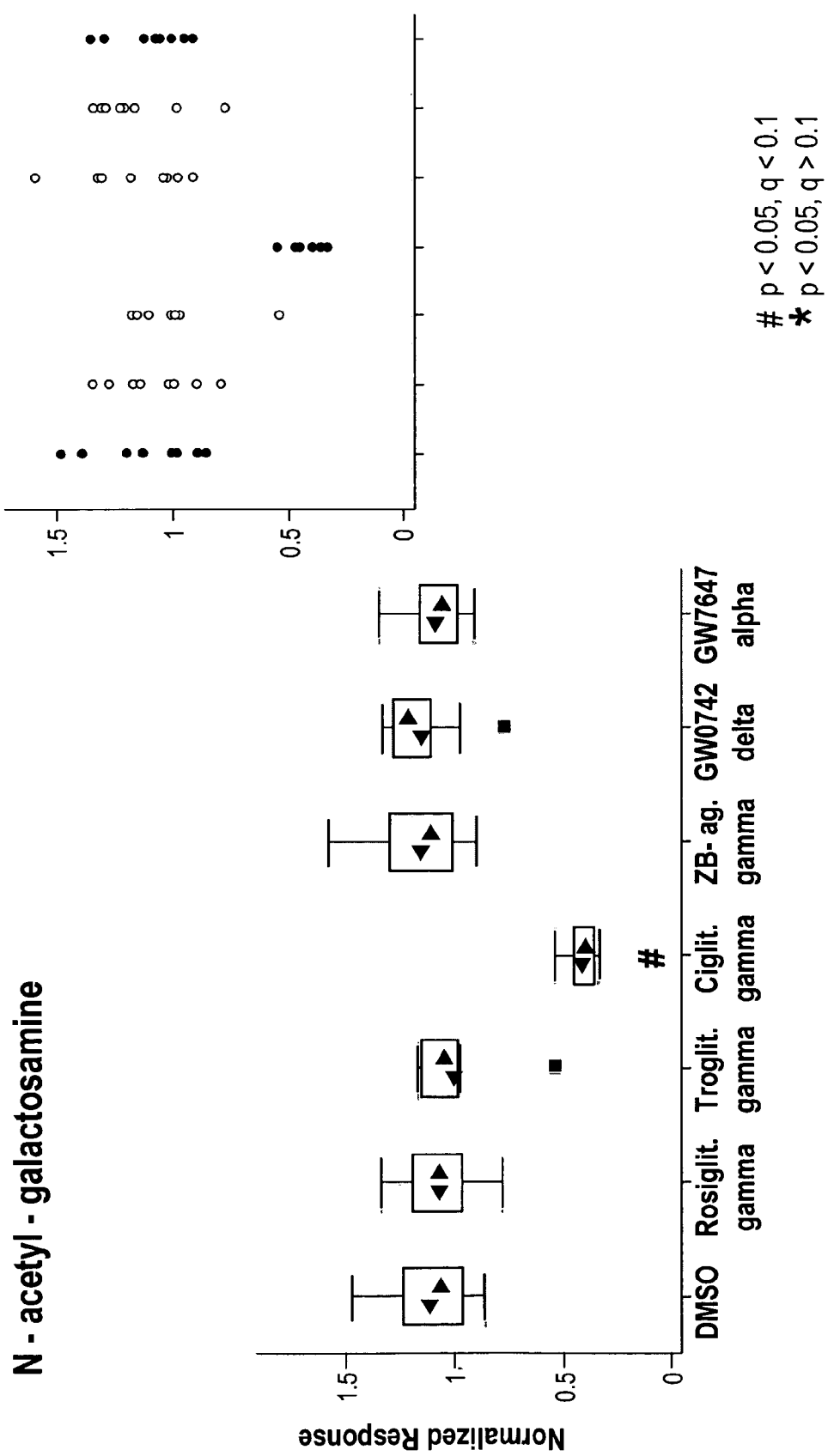
FIG. 10 is a graph which shows comparative levels of N-acetyl-galactosamine for six drugs.

FIG. 7 is a graph which shows the effect of the six compounds on aspartate levels. The levels of aspartate were most increased by Troglitzone. FIG. 8 is a graph which shows the effect of the six compounds on threonine levels. FIG. 9 is a graph which shows the effect of the six compounds on amounts of pantothenic acid. The levels of pantothenic acid were most increased by Troglitzone. FIG. 10 is a graph which shows the effect of the six compounds on N-acetyl-galactosamine. The levels of N-acetyl-galactosamine were most decreased by Ciglitazone.

In general, a number of metabolites including the individual fatty acids making up the total free fatty acid measurement, amino-acids, and amino acid catabolism metabolites were altered upon drug treatment in line with the mechanism of action for these drugs. However, a number of compounds showed differing levels of what are potential off-target interactions. The data also demonstrates in vitro cell culture results can be predictive of in vivo effects with an accurate metabolomics analysis.

Example 3

Metabolomic Analysis of Test Compounds

The cell cultures used in this example were performed according to standard protocols with the cells in 10% FCS. Three test compounds (ATV, DRV, and LPV) and one control (DMSO) were tested at a dosage of 30 µM on cultures of HepG2 and adipocyte cells. The adipocytes were human and fully differentiated. Table 6 shows the percent relative standard deviation (RSD) for the control matrix (CMTRX), DMSO, ATV, DRV, and LPV. In the hepatocyte culture, 503 compounds were identified. Of these compounds, 209 compounds were named (42%). In the adipocyte culture, 391 compounds were identified and 173 were named (44%).

TABLE 6

| | Hepatocytes | | Adipocytes | |
|---|---|---|---|---|
| | Overall | n | Overall | n |
| CMTRX | 16% | 436 | 14% | 320 |
| DMSO | 21% | 326 | 23% | 246 |
| ATV | 24% | 326 | 22% | 246 |
| DRV | 21% | 326 | 25% | 246 |
| LPV | 20% | 326 | 21% | 246 |

The number of compounds affected in each culture by each test compound are shown in Table 7. Compounds which are significantly effected are defined for this example as compounds with a p<0.01.

TABLE 7

| | ATV | DRV | LPV |
|---|---|---|---|
| | Hepatocytes | | |
| Total p < 0.01 | 71 | 69 | 131 |
| # increased | 16 | 46 | 104 |
| # decreased | 55 | 23 | 27 |
| | Primary Adipocytes | | |
| Total p < 0.01 | 87 | 22 | 99 |
| # increased | 32 | 7 | 53 |
| # decreased | 55 | 15 | 46 |

The target of the agent is not present in the cell cultures assayed, thus the changed compounds for each culture represent off-target effects, and therefore, the number of changed compounds can be used to generate a score that can be used as one criteria to rank the test compounds. Using the hepatocyte cultures, ATV and DRV are roughly equivalent and LPV is the least desirable. Using the adipocyte cultures, DRV is the most desirable, followed by ATV and LPV.

The data is also shown graphically in the Z-plots shown in FIG. 11. The figures show data for the DMSO control, ATV, DRV, and LPV. The conrol data is illustrated in black circles and clusters around 0. The open circles represent ATV, DRV and LPV and the plots are labeled as to each compound/DMSO comparison. The Z-plots graphically represent Z-scores. The z score for an item, indicates how far and in what direction, that item deviates from its distribution's mean, expressed in units of its distribution's standard deviation. The mathematics of the z score transformation are such that if every item in a distribution is converted to its z score, the transformed scores will necessarily have a mean of zero and a standard deviation of one. The z score transformation is especially useful when seeking to compare the relative standings of items from distributions with different means and/or different standard deviations. The zero on the horizontal axis represents the mean and the remaining numbers on the horizontal axis represent standard deviations (+/−) from the mean. Each dot represents the level of a single compound for an individual sample in the data set. A Gaussian distribution of the data is shown by the fact that 95% of the data points fall within 2 standard deviations (+/−) from the mean. In one embodiment, the information from the z-scores is used to generate scores which may be included in a report ranking the test compounds, as shown in FIG. 4.

FIGS. 12A-12G shows a sample output for the test compounds. It shows which metabolites in each pathway were modulated by each of the test compounds. The values in the FIGS. 12A-12G are the ratios of metabolites present in the test compound cultures as compared to the control. Red indicates that the metabolite is elevated relative to control and green indicates that the metabolite is decreased relative to control. The summary shown in FIGS. 12H-12I outlines potential biological effects of the test compounds.

Equivalents

Those skilled in the art will recognize, or be able to ascertain using no more than routine experimentation, many equivalents to the specific embodiments and methods described herein. Such equivalents are intended to be encompassed by the scope of the following claims. The entire contents of all references and patents cited herein are hereby incorporated by reference.

The invention claimed is:

1. A method for identifying biochemical pathways affected by an agent comprising:
    obtaining a small molecule profile of a sample from an assay treated with said agent, said small molecule profile comprising information regarding at least ten small molecules including identification information for the at least ten small molecules;
    comparing said small molecule profile to a standard small molecule profile;
    identifying components of said small molecule profile affected by said agent;
    identifying one or more biochemical pathways associated with said identified components by mapping said identified components to the one or more biochemical pathways using a collection of data describing a plurality of biochemical pathways and an analysis facility executing on a processor of a computing device, thus identifying biochemical pathways affected by said agent, wherein the plurality of biochemical pathways includes the one or more identified biochemical pathways associated with the identified components and a plurality of non-identified biochemical pathways; and
    storing information regarding each identified biochemical pathway and an identified component or identified components mapped to the identified biochemical pathway for each identified biochemical pathway.

2. The method of claim 1, wherein said agent is a toxin.

3. The method of claim 1, wherein said agent is a therapeutic agent.

4. The method of claim 3, wherein said therapeutic agent is a therapeutic agent used for the treatment of a metabolic, immunological, neurological, oncological, viral, or other disorder.

5. The method of claim 1, wherein said assay comprises administering the agent to a subject.

6. The method of claim 1, wherein said assay comprises administering the agent in vitro.

7. The method of claim 1, wherein said small molecule profiles are obtained using one or more of the following: HPLC, TLC, electrochemical analysis, mass spectroscopy, refractive index spectroscopy (RI), Ultra-Violet spectroscopy (UV), fluorescent analysis, radiochemical analysis, Near-InfraRed spectroscopy (Near-IR), Nuclear Magnetic Resonance spectroscopy (NMR), and Light Scattering analysis (LS).

8. A method for identifying biochemical pathways affected by an agent, comprising:
    administering an agent to a subject;
    obtaining a post-administration sample from said subject;
    detecting a small molecule profile of the post-administration sample, said post-administration small molecule profile comprising information regarding at least ten small molecules including identification information for the at least ten small molecules;
    identifying components of said post-administration small molecule profile affected by said agent;
    identifying one or more biochemical pathways associated with said identified components to biochemical pathways by mapping said identified components to the one or more biochemical pathways using a collection of data describing a plurality of biochemical pathways and an analysis facility executing on a processor of a computing device, thus identifying biochemical pathways affected by said agent, wherein the plurality of biochemical pathways includes the one or more identified biochemical pathways associated with the identified components and a plurality of non-identified biochemical pathways; and
    displaying information regarding each identified biochemical pathway and an identified component or identified components mapped to the identified biochemical pathway for each identified biochemical pathway on a display of a computing device.

9. The method of claim 8, wherein said agent is a therapeutic agent.

10. The method of claim 8, wherein said agent is a peptidomimetic, protein, peptide, nucleic acid, or small molecule.

11. A method for positioning an agent comprising:
    obtaining a small molecule profile of a sample from an assay treated with said agent, said small molecule profile comprising information regarding at least ten small molecules including identification information for the at least ten small molecules;
    comparing said small molecule profile to a standard small molecule profile;
    identifying components of said small molecule profile affected by said agent;
    identifying one or more biochemical pathways associated with said identified components by mapping said identified components to the one or more biochemical pathways using a collection of data describing a plurality of biochemical pathways and an analysis facility executing on a processor of a computing device, wherein the plurality of biochemical pathways includes the one or more identified biochemical pathways associated with the identified components and a plurality of non-identified biochemical pathways;
    storing information regarding each identified biochemical pathway and an identified component or identified components associated with the identified biochemical pathway for each identified biochemical pathway; and
    using said stored information regarding said one or more identified biochemical pathways to identify a therapeutic use for the compound, thus positioning the agent.

12. The method of claim 11, wherein said agent is positioned to minimize unexpected effects of said agent.

13. The method of claim 11, wherein said agent is positioned to maximize therapeutic effects of said agent.

14. A system for the development of lead compounds, comprising:
    a collection of data describing a plurality of biochemical pathways, each biochemical pathway description specifying small molecule compounds associated with the biochemical pathway;
    a data acquisition apparatus, the data acquisition apparatus processing an assay following the addition of an agent to the assay in order to determine the effect of the agent on the assay, the processing of the assay generating result data indicating a condition of a small molecule compound in the assay relative to a control for each of a plurality of small molecule compounds, wherein the plurality of small molecule compounds comprises at least ten small molecule compounds; and an analysis facility executing on a computing device to identify one or more biochemical pathways affected by the indicated condition for at least some of the plurality of small molecule compounds by mapping said at least some of the plurality of small molecule compounds to the one or more biochemical pathways using the collection of data describing the plurality of biochemical pathways, wherein the one or more identified biochemical pathways comprise only a portion of the plurality of biochemical pathways described by the collection of data, the analysis facility used to store information regarding each identified biochemical pathway and a small molecule compound or small molecule compounds mapped to the identified biochemical pathway for each identified biochemical pathway.

15. The system of claim 14 wherein the analysis facility generates a score ranking the at least some of the plurality of small molecule compounds based on a change in the one or more identified biochemical pathways affected by the indicated conditions.

16. The system of claim 14, wherein the analysis facility is used in identifying at least one expected effect in the one or more biochemical pathways affected by the indicated condition for said at least some of the plurality of small molecule compounds.

17. The system of claim 14, wherein the analysis facility is used in identifying at least one unexpected effect in the one or more biochemical pathways affected by the indicated condition for said at least some of the plurality of small molecule compounds.

18. The system of claim 17 wherein the unexpected effect is a negative unexpected effect.

19. The system of claim 14, further comprising:
a display device, the display device displaying a listing of the one or more biochemical pathways affected by the indicated condition for said at least some of the plurality of small molecule compounds.

20. The system of claim 19, wherein the listing identifies at least one changed metabolite in the one or more biochemical pathways affected by the indicated condition for said at least some of the plurality of small molecule compounds.

21. The system of claim 14, wherein the data acquisition apparatus performs at least one of liquid chromatography, gas chromatography, mass spectrometry, liquid chromatography-mass spectrometry or gas chromatography-mass spectrometry on the assay.

22. The system of claim 14, wherein the analysis facility is used to interpret a meaning of a change in the one or more biochemical pathways affected by the indicated condition for said at least some of the plurality of small molecule compounds, the interpretation based on a pre-defined set of criteria.

23. The system of claim 22, wherein the interpretation is displayed to a user.

24. The system of claim 22, wherein the interpretation is stored.

25. The system of claim 14, wherein the assay is an in vitro assay.

26. The system of claim 14, wherein the assay is an in vivo assay.

27. The system of claim 14, wherein the collection of data is stored in a database.

28. A method of identifying lead compounds, comprising:
providing, in a computing device, a collection of data describing a plurality of biochemical pathways, each biochemical pathway description specifying small molecule compounds associated with the biochemical pathway;
adding an agent to an assay;
processing the assay to acquire result data indicating the effect of the addition of the agent on the assay, the result data indicating a condition of at least one small molecule compound in the assay relative to a control for each of a plurality of small molecule compounds, wherein the plurality of small molecule compounds comprises at least ten small molecule compounds;
identifying, using an analysis facility executing on a processor of a computing device, one or more biochemical pathways affected by the indicated condition for at least some of the plurality of small molecule compounds, the identifying including mapping said at least some of the plurality of small molecule compounds to the one or more biochemical pathways using the collection of data describing the plurality of biochemical pathways, wherein the one or more identified biochemical pathways comprise only a portion of the plurality of biochemical pathways described by the collection of data; and
storing information regarding each identified biochemical pathway and a small molecule compound or small molecule compounds mapped to the identified biochemical pathway for each identified biochemical pathway.

29. The method of claim 28, wherein the identification identifies at least one expected effect in the one or more biochemical pathways affected by the indicated condition for said at least some of the plurality of small molecule compounds.

30. The method of claim 29, further comprising:
displaying a listing of the one or more biochemical pathways affected by the indicated condition for said at least some of the plurality of small molecule compounds.

31. The method of claim 29, wherein the listing identifies at least one changed metabolite in the one or more biochemical pathways affected by the indicated condition for said at least some of the plurality of small molecule compounds.

32. The method of claim 29, wherein the processing further comprises:
performing at least one of liquid chromatography, gas chromatography, mass spectrometry, liquid chromatography-mass spectrometry or gas chromatography-mass spectrometry on the assay.

33. The method of claim 29, further comprising:
interpreting a meaning of a change in the one or more biochemical pathways affected by the indicated condition for said at least some of the plurality of small molecule compounds, the interpretation based on a pre-defined set of criteria.

34. The method of claim 33, further comprising:
displaying the interpretation to a user.

35. The method of claim 33, further comprising:
storing the interpretation of the meaning of the change in the one or more biochemical pathways affected by the indicated condition for said at least some of the plurality of small molecule compounds.

36. The method of claim 29, wherein the assay is an in vitro assay.

37. The method of claim 29, wherein the assay is an in vivo assay.

38. The method of claim 29, wherein the collection of data describing a plurality of biochemical pathways is stored in a database.

39. The method of claim 28, wherein the identification identifies at least one unexpected effect in the one or more biochemical pathways affected by the indicated condition for at least some of the plurality of small molecule compounds.

40. The method of claim 28 wherein the unexpected effect is a negative unexpected effect.

41. A medium for use with a computing device, the medium holding computer-executable instructions for identifying lead compounds, the instructions comprising:
 instructions for providing, in a computing device, a collection of data describing a plurality of biochemical pathways, each biochemical pathway description specifying small molecule compounds associated with the biochemical pathway;
 instructions for adding an agent to an assay;
 instructions for processing the assay to acquire result data indicating the effect of the addition of the agent on the assay, the result data indicating a condition of a small molecule compound in the assay relative to a control for each of a plurality of small molecule compounds, wherein the plurality of small molecule compounds comprises at least ten small molecule compounds;
 instructions for identifying, one or more biochemical pathways affected by the indicated condition for at least some of the plurality of small molecule compounds, the identifying including mapping said at least some of the plurality of small molecule compounds to the one or more biochemical pathways using the collection of data describing the plurality of biochemical pathways, wherein the identified biochemical pathway or pathways comprise only a portion of the plurality of biochemical pathways described by the collection of data; and
 instructions for storing information regarding each identified biochemical pathway and a small molecule compound or small molecule compounds mapped to the identified biochemical pathway for each identified biochemical pathway.

42. The medium of claim 41, wherein the identification identifies at least one expected effect in the one or more biochemical pathways affected by the indicated condition for said at least some of the plurality of small molecule compounds.

43. The medium of claim 41, wherein the identification identifies at least one unexpected effect in the one or more biochemical pathways affected by the indicated condition for said at least some of the plurality of small molecule compounds.

44. The medium of claim 41 wherein the unexpected effect is a negative unexpected effect.

45. The medium of claim 41, wherein said instructions further comprise:
 instructions for displaying a listing of the one or more biochemical pathways affected by the indicated condition for said at least some of the plurality of small molecule compounds.

46. The medium of claim 41, wherein the listing identifies at least one changed metabolite in the one or more biochemical pathways affected by the indicated condition for said at least some of the plurality of small molecule compounds.

47. The medium of claim 41, wherein the instructions for processing further comprise:
 instructions for performing at least one of liquid chromatography, gas chromatography, mass spectrometry, liquid chromatography-mass spectrometry or gas chromatography-mass spectrometry on the assay.

48. The medium of claim 41, wherein the instructions further comprise:
 instructions for interpreting a meaning of a change in the one or more biochemical pathways affected by the indicated condition for said at least some of the plurality of small molecule compounds, the interpretation based on a pre-defined set of criteria.

49. The medium of claim 48 wherein the instructions further comprise:
 instructions for displaying the interpretation to a user.

50. The medium of claim 48, wherein the instructions further comprise:
 instructions for storing the interpretation of the meaning of the change in the one or more biochemical pathways affected by the indicated condition for said at least some of the plurality of small molecule compounds.

51. The medium of claim 41, wherein the assay is an in vitro assay.

52. The medium of claim 41, wherein the assay is an in vivo assay.

53. The medium of claim 41, wherein the collection of data describing a plurality of biochemical pathways is stored in a database.

54. A method of identifying lead compounds, comprising:
 providing, in a computing device, a collection of data describing a plurality of biochemical pathways, each biochemical pathway description specifying small molecule compounds associated with the biochemical pathway;
 adding an agent to an assay;
 processing the assay to acquire result data indicating the effect of the addition of the agent on the assay, the result data indicating a condition of a small molecule compound in the assay relative to a control for each of a plurality of small molecule compounds, wherein the plurality of small molecule compounds comprises at least ten small molecule compounds;
 identifying programmatically without user assistance, using an analysis facility executing on a processor of a computing device, one or more biochemical pathways affected by the indicated condition for at least some of the plurality of small molecule compounds by mapping said at least some of the plurality of small molecule compounds to the one or more biochemical pathways using the collection of data describing the plurality of biochemical pathways, wherein the one or more identified biochemical pathways comprise only a portion of the plurality of biochemical pathways described by the collection of data; and
 storing information regarding each identified biochemical pathway and a small molecule compound or small molecule compounds mapped to the identified biochemical pathway for each identified biochemical pathway.

55. The method of claim 54, further comprising:
 interpreting programmatically without user assistance a meaning of a change in the one or more biochemical pathways affected by the indicated condition for said at least some of the plurality of small molecule compounds, the interpretation based on a pre-defined set of criteria.

56. A medium for use with a computing device, the medium holding instructions for identifying lead compounds, comprising:
 providing, in a computing device, a collection of data describing a plurality of biochemical pathways, each biochemical pathway description specifying small molecule compounds associated with the biochemical pathway;
 adding an agent to an assay;

processing the assay to acquire result data indicating the effect of the addition of the agent on the assay, the result data indicating a condition of a small molecule compound in the assay relative to a control for each of a plurality of small molecule compounds, wherein the plurality of small molecule compounds comprises at least ten small molecule compounds;

identifying programmatically without user assistance, one or more biochemical pathways affected by the indicated condition for at least some of the plurality of small molecule compounds by mapping said at least some of the plurality of small molecule compounds to the one or more biochemical pathways using the collection of data describing the plurality of biochemical pathways, wherein the one or more identified biochemical pathways comprise only a portion of the plurality of biochemical pathways described by the collection of data; and storing information regarding each identified biochemical pathway and a small molecule compound or small molecule compounds mapped to the identified biochemical pathway for each identified biochemical pathway.

57. The medium of claim 56 wherein the instructions further comprise:

instructions for interpreting programmatically without user assistance, a meaning of a change in the one or more biochemical pathways affected by the indicated condition for said at least some of the plurality of small molecule compounds, the interpretation based on a predefined set of criteria.

58. A method for determining an advantageous dose of an agent, comprising:

obtaining a first small molecule profile of a sample from a subject treated with a first dose of said agent, said first small molecule profile comprising information regarding at least ten small molecules including identification information for the at least ten small molecules;

obtaining a second small molecule profile of a sample from a second subject treated with a second dose of said agent;

comparing said first small molecule profile to said second small molecule profile;

identifying components of said small molecule profiles affected by the dose of said agent;

identifying one or more biochemical pathways associated with said identified components by mapping said identified components to the one or more biochemical pathways using a collection of data describing a plurality of biochemical pathways and an analysis facility executing on a processor of a computing device wherein the plurality of biochemical pathways includes the one or more identified biochemical pathways associated with the identified components and a plurality of non-identified biochemical pathways;

storing information regarding each identified biochemical pathway an identified component or identified components mapped to the identified biochemical pathway for each identified biochemical pathway; and using the stored information regarding said one or more identified biochemical pathways to identify an advantageous dose, thus determining an advantageous dose of said agent.

59. The method of claim 58, wherein said first and second subjects are the same subject.

60. The method of claim 58, wherein said advantageous dose is selected to minimize off target effects of said agent.

61. The method of claim 58, wherein said advantageous dose is selected to maximize on target effects of said agent.

62. The method of claim 58, wherein said first and second subjects are human.

63. The method of claim 62, additionally comprising obtaining further small molecule profiles at additional doses of the agent.

64. A method for determining an advantageous salt form of an agent, comprising:

obtaining a first small molecule profile of a sample from a subject treated with a first salt form of said agent, said first small molecule profile comprising information regarding at least ten small molecules including identification information for the at least ten small molecules;

obtaining a second small molecule profile of a sample from a second subject treated with a second salt form of said agent;

comparing said first small molecule profile to said second small molecule profile;

identifying components of said small molecule profiles affected by the salt form of said agent;

identifying one or more biochemical pathways associated with said identified components by mapping said identified components to the one or more biochemical pathways using a collection of data describing a plurality of biochemical pathways and an analysis facility executing on a processor of a computing device, wherein the plurality of biochemical pathways includes the one or more identified biochemical pathways associated with the identified components and a plurality of non-identified biochemical pathways;

storing information regarding each identified biochemical pathway and an identified component or identified components mapped to the identified biochemical pathway for each identified biochemical pathway; and using the stored information regarding said one or more identified biochemical pathways to identify an advantageous salt form, thus determining an advantageous salt form of said agent.

65. The method of claim 64, wherein said first and second subjects are the same subject.

66. The method of claim 64, wherein said advantageous salt form is selected to minimize off target effects of said agent.

67. The method of claim 64, wherein said advantageous salt form is selected to maximize on target effects of said agent.

68. The method of claim 64, wherein said first and second subjects are human.

69. The method of claim 64, additionally comprising obtaining further small molecule profiles using one or more additional salt forms of the agent.

70. The method of claim 64, wherein said salt forms are pharmaceutically acceptable salt forms.

71. The method of claim 70, wherein said pharmaceutically acceptable salt forms are selected from the group consisting of: hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, laurylsulphonate salts, hydroxide, carbonate, ammonia salts, organic primary, secondary or tertiary amine salts, lithium, sodium, potassium, calcium, magnesium, aluminum salts, ethylamine, diethylamine, ethylenediamine, ethanolamine, diethanolamine, and piperazine.

72. A method for determining an advantageous prodrug form of an agent, comprising:

obtaining a first small molecule profile of a sample from a subject treated with a first prodrug form of said agent, said first small molecule profile comprising information regarding at least ten small molecules including identification information for the at least ten small molecules;

obtaining a second small molecule profile of a sample from a second subject treated with a second prodrug form of said agent;

comparing said first small molecule profile to said second small molecule profile;

identifying components of said small molecule profiles affected by the prodrug form of said agent;

identifying one or more biochemical pathways associated with said identified components by mapping said identified components to the one or more biochemical pathways using a collection of data describing a plurality of biochemical pathways and an analysis facility executing on a processor of a computing device, wherein the plurality of biochemical pathways includes the one or more identified biochemical pathways associated with the identified components and a plurality of non-identified biochemical pathways;

storing information regarding each identified biochemical pathway and an identified component or identified components mapped to the identified biochemical pathway for each identified biochemical pathway; and using the stored information regarding said one or more identified biochemical pathways to identify an advantageous prodrug form, thus determining an advantageous prodrug form of said agent.

73. The method of claim 72, wherein said first and second subjects are the same subject.

74. The method of claim 72, wherein said advantageous prodrug form is selected to minimize off target effects of said agent.

75. The method of claim 72, wherein said advantageous prodrug form is selected to maximize on target effects of said agent.

76. The method of claim 72, wherein said first and second subjects are human.

77. The method of claim 72, additionally comprising obtaining further small molecule profiles using one or more additional prodrug forms of the agent.

78. A method for determining an advantageous formulation of an agent, comprising:

obtaining a first small molecule profile of a sample from a first subject treated with a first formulation of said agent, said first small molecule profile comprising information regarding at least ten small molecules including identification information for the at least ten small molecules;

obtaining a second small molecule profile of a sample from a second subject treated with a second formulation of said agent;

comparing said first small molecule profile to said second small molecule profile;

identifying components of said small molecule profiles affected by the formulation of said agent;

identifying one or more biochemical pathways associated with said identified components by mapping said identified components to the one or more biochemical pathways using a collection of data describing a plurality of biochemical pathways and an analysis facility executing on a processor of a computing device, wherein the plurality of biochemical pathways includes the one or more identified biochemical pathways associated with the identified components and a plurality of non-identified biochemical pathways;

storing information regarding each identified biochemical pathway and an identified component or identified components mapped to the identified biochemical pathway for each identified biochemical pathway; and using the stored information regarding said one or more identified biochemical pathways to identify an advantageous pharmaceutical formulation, thus determining an advantageous formulation of said agent.

79. The method of claim 78, wherein said first and second subjects are the same subject.

80. The method of claim 78, wherein said advantageous formulation is selected to minimize off target effects of said agent.

81. The method of claim 78, wherein said advantageous formulation is selected to maximize on target effects of said agent.

82. The method of claim 78, wherein said first and second subjects are human.

83. The method of claim 78, additionally comprising obtaining further small molecule profiles using one or more additional formulations of the agent.

84. The method of claim 78, wherein said formulations are formulated for oral, nasal, topical, transdermal, buccal, sublingual, rectal, vaginal or parenteral administration.

85. The method of claim 78, wherein said first and second formulations comprise the same or different pharmaceutically effective carriers.

86. A method for determining an advantageous route of administration of an agent, comprising:

obtaining a first small molecule profile of a sample from a first subject treated with an agent administered using a first route of administration, said first small molecule profile comprising information regarding at least ten small molecules including identification information for the at least ten small molecules;

obtaining a second small molecule profile of a sample from a second subject treated with said agent administered using a second route of administration;

comparing said first small molecule profile to said second small molecule profile;

identifying components of said small molecule profiles affected by the route of administration of said agent;

identifying one or more biochemical pathways associated with said identified components by mapping said identified components to the one or more biochemical pathways using a collection of data describing a plurality of biochemical pathways and an analysis facility executing on a processor of a computing device wherein the plurality of biochemical pathways includes the one or more identified biochemical pathways associated with the identified components and a plurality of non-identified biochemical pathways;

storing information regarding each identified biochemical pathway and an identified component or identified components mapped to the identified biochemical pathway for each identified biochemical pathway; and using the stored information regarding said one or more identified biochemical pathways to identify an advantageous route of administration, thus determining an advantageous route of administration of said agent.

87. The method of claim 86, wherein said first and second subjects are the same subject.

88. The method of claim 86, wherein said advantageous route of administration is selected to minimize off target effects of said agent.

89. The method of claim 86, wherein said advantageous route of administration is selected to maximize on target effects of said agent.

90. The method of claim 86, wherein said first and second subjects are human.

91. The method of claim 86, additionally comprising obtaining further small molecule profiles using one or more additional routes of administration of the agent.

92. The method of claim 86, wherein said routes of administration are selected from the group consisting of: oral, nasal, topical, transdermal, buccal, sublingual, rectal, vaginal and parenteral administration.

93. A method for determining an advantageous therapeutic window of an agent, comprising:
 obtaining a first small molecule profile of a sample from a first subject treated with an agent at a first stage of a disease state, said first small molecule profile comprising information regarding at least ten small molecules including identification information for the at least ten small molecules;
 obtaining a second small molecule profile of a sample from a second subject treated with said agent at a second stage of a disease state;
 comparing said first small molecule profile to said second small molecule profile;
 identifying components of said small molecule profiles affected by the stage of the disease state at which the agent was administered;
 identifying one or more biochemical pathways associated with said identified components by mapping said identified components to the one or more biochemical pathways using a collection of data describing a plurality of biochemical pathways and an analysis facility executing on a processor of a computing device, wherein the plurality of biochemical pathways includes the one or more identified biochemical pathways associated with the identified components and a plurality of non-identified biochemical pathways;
 storing information regarding each identified biochemical pathway and an identified component or identified components mapped to the identified biochemical pathway for each identified biochemical pathway; and
 using the stored information regarding said one or more identified biochemical pathways to identify an advantageous therapeutic window for said agent.

94. The method of claim 93, wherein said first and second subjects are the same subject.

95. The method of claim 93, wherein said advantageous route of administration is selected to minimize off target effects of said agent.

96. The method of claim 93, wherein said advantageous route of administration is selected to maximize on target effects of said agent.

97. The method of claim 93, wherein said first and second subjects are human.

98. The method of claim 93, additionally comprising obtaining further small molecule profiles using one or more additional routes of administration of the agent.

99. The method of claim 93, wherein said routes of administration are selected from the group consisting of: oral, nasal, topical, transdermal, buccal, sublingual, rectal, vaginal and parenteral administration.

100. A method for determining an advantageous alternate form of an agent, comprising:
 obtaining a first small molecule profile of a sample from a subject treated with a first alternate of the agent, the small molecule profile comprising information regarding at least ten small molecules including identification information for the at least ten small molecules;
 obtaining a second small molecule profile of a sample from a second subject treated with a second alternate form of the agent;
 comparing the first small molecule profile to the second small molecule profile; identifying components of the small molecule profiles affected by the alternate form of the agent;
 identifying one or more biochemical pathways associated with the identified components by mapping said identified components to the one or more biochemical pathways using a collection of data describing a plurality of biochemical pathways and an analysis facility executing on a processor of a computing device, wherein the plurality of biochemical pathways includes the one or more identified biochemical pathways associated with the identified components and a plurality of non-identified biochemical pathways;
 storing information regarding each identified biochemical pathway and an identified component or identified components mapped to the identified biochemical pathway for each identified biochemical pathway; and
 using the stored information regarding said one or more identified biochemical pathways to identify an advantageous alternate form, thus determining an advantageous alternate form of the agent.

101. The method of any one of claims 1, 8, 11, 58, 64, 72, 78, 86, 93, and 100, wherein each of the at least 10 small molecules has a molecular weight that is not over 1,000.

102. The method of any one of claims 1, 8, 11, 14, 28, 41, 54, 56, 58, 64, 72, 78, 86, 93, and 100, wherein at least one identified biochemical pathway is selected from a group consisting of:
 carbohydrate metabolism, glycolysis, biosynthesis, gluconeogenesis, Kreb's Cycle, Citric Acid Cycle, TCA Cycle, pentose phosphate pathway, glycogen biosynthesis, galactose pathway, Calvin Cycle, aminosugars metabolism, butanoate metabolism, pyruvate metabolism, fructose metabolism, mannose metabolism, inositol phosphate metabolism, propanoate metabolism, starch and sucrose metabolism, energy metabolism, oxidative phosphorylation, reductive carboxylate cycle, lipid metabolism, triacylglycerol metabolism, activation of fatty acids, β-oxidation of polyunsaturated fatty acids, β-oxidation of other fatty acids, α-oxidation pathway, de novo biosynthesis of fatty acids, cholesterol biosynthesis, bile acid biosynthesis, fatty acid metabolism, glycerolipid metabolism, glycerophospholipid metabolism, sphingolipid metabolism, amino acid metabolism, glutamate reactions, Kreb-Henseleit urea cycle, shikimate pathway, phenylalanine and tyrosine biosynthesis, tryptophan biosynthesis, metabolism and/or degradation of any of the following amino acids: alanine, aspartate, arginine, proline, glutamate, glycine, serine, threonine, histadine, cysteine, methionine, phenylalanine, tryptophan, tyrosine, valine, leucine, and isoleucine, biosynthesis of amino acids, lysine biosynthesis, tryptophan biosynthesis, folate biosynthesis, one carbon pool by folate, pantothenate and CoA biosynthesis, riboflavin metabolism, thiamine metabolism, vitamin B6 metabolism, β-alanine methabolism, D-glutamine and D-glutamate metabolism, glutathionine metabolism, cyanoamino acid metabolism, N-glycan biosynthesis, benzoate degradation, alkaloid biosynthesis, selenoamino acid metabolism, purine metabolism, pyrimidine metabolism, phosphatidylinositol signaling system, neuroacive ligand-receptor interaction, energy metabolism, oxidative phosphorylation, ATP synthesis, photosynthesis, methane metabolism, phosphogluconate pathway, oxidation-reduction, electron transport, oxidative phosphorylation, respiratory metabolism, HMG-CoA reductase pathway, porphyrin synthesis pathway (heme synthesis), nitrogen metabolism (urea cycle), nucleotide biosynthesis, and DNA replication, transcription, and translation.

* * * * *